US007876913B2

(12) United States Patent
Kobayashi et al.

(10) Patent No.: US 7,876,913 B2

(45) Date of Patent: Jan. 25, 2011

(54) APPARATUS FOR PRODUCING SOUND EFFECT FOR MOBILE OBJECT

(75) Inventors: Yasunori Kobayashi, Utsunomiya (JP); Toshio Inoue, Tochigi-ken (JP); Akira Takahashi, Tochigi-ken (JP); Kosuke Sakamoto, Utsunomiya (JP)

(73) Assignee: Honda Motor Co., Ltd., Tokyo (JP)

( * ) Notice: Subject to any disclaimer, the term of this patent is extended or adjusted under 35 U.S.C. 154(b) by 1344 days.

(21) Appl. No.: 11/384,268

(22) Filed: Mar. 21, 2006

(65) Prior Publication Data

US 2006/0215846 A1 Sep. 28, 2006

(30) Foreign Application Priority Data

Mar. 22, 2005 (JP) ............................ 2005-081075
Feb. 27, 2006 (JP) ............................ 2006-049642

(51) Int. Cl.
*H04B 1/00* (2006.01)
*A61F 11/06* (2006.01)
*G10K 11/16* (2006.01)
*H03B 29/00* (2006.01)

(52) U.S. Cl. ....................... 381/86; 381/71.1; 381/71.4; 381/71.14; 381/94.1

(58) Field of Classification Search .................. 381/86, 381/94.1, 71.1-71.2, 71.4, 71.8-71.14; 180/206
See application file for complete search history.

(56) References Cited

U.S. PATENT DOCUMENTS

| | | | | |
|---|---|---|---|---|
| 4,549,289 | A | | 10/1985 | Schwartz et al. |
| 5,359,662 | A | * | 10/1994 | Yuan et al. ............... 381/71.14 |
| 5,426,703 | A | | 6/1995 | Hamabe et al. |
| 5,485,523 | A | * | 1/1996 | Tamamura et al. ......... 381/71.4 |
| 2004/0219981 | A1 | | 11/2004 | Bando |
| 2004/0252844 | A1 | | 12/2004 | Christensen et al. |

FOREIGN PATENT DOCUMENTS

| | | | |
|---|---|---|---|
| DE | 197 46 523 | A1 | 5/1998 |
| DE | 199 11 335 | A1 | 9/2000 |
| DE | 199 45 259 | C1 | 1/2001 |
| JP | 54-8027 | | 1/1979 |
| JP | 4-504916 | A | 8/1992 |
| JP | 05-008694 | A | 1/1993 |
| JP | 05-080790 | A | 4/1993 |
| JP | 10-206180 | A | 8/1998 |
| JP | 11-212581 | A | 8/1999 |
| JP | 2001-119800 | A | 4/2001 |
| JP | 2004-329290 | | 11/2004 |
| WO | 90/13109 | A1 | 11/1990 |

* cited by examiner

*Primary Examiner*—Vivian Chin
*Assistant Examiner*—Douglas J Suthers
(74) *Attorney, Agent, or Firm*—Arent Fox LLP

(57) ABSTRACT

Gain characteristics depending on the frequency of a reference signal from speakers to a passenger position in a motor vehicle, i.e., gain characteristics which are an inversion of vehicle cabin sound field characteristics, are set in a first acoustic corrector. At the passenger position, a gain characteristic curve that is flat at various frequencies is achieved to prevent gain peaks and dips from occurring at the passenger position. A sound effect generated at the passenger position is made linear depending on the state of a noise source, or more specifically, a noise source caused by an accelerating action on the motor vehicle.

11 Claims, 17 Drawing Sheets

16

| ADDRESS | WAVEFORM DATA |
|---|---|
| 0 | 0 |
| 1 | $A\sin(360° \times \frac{1}{N})$ |
| ••• | ••• |
| i | $A\sin(360° \times \frac{i}{N})$ |
| ••• | ••• |
| N | $A\sin(360° \times \frac{N-1}{N})$ |

102

APPARATUS FOR PRODUCING SOUND EFFECT FOR MOBILE OBJECT

BACKGROUND OF THE INVENTION

1. Field of the Invention

The present invention relates to an apparatus for producing a sound effect in a mobile object depending on the rotational speed of an engine mounted on the mobile object, and more particularly to a mobile object sound effect producing apparatus which is suitable for use on motor vehicles such as passenger automobiles, aircraft such as helicopters, air planes, etc., or watercrafts such as pleasure boats, etc.

2. Description of the Related Art

Heretofore, there have been proposed in the art sound effect producing apparatus for detecting an accelerating or decelerating action made by a passenger (driver) on a mobile object, e.g., a motor vehicle, and producing and radiating a sound effect depending on the acceleration or deceleration through a speaker installed in a vehicle cabin into the vehicle cabin, as disclosed in Japanese Laid-Open Patent Publication Nos. 54-8027 and 4-504916 (PCT).

According to the disclosed sound effect producing apparatus, when the rotational speed of the engine mounted on the motor vehicle increases in response to an accelerating action made by the passenger, a sound effect having a high frequency and a large sound level is generated depending on the increase in the engine rotational speed, and the sound effect is radiated from the speaker into the vehicle cabin to create a staged sound atmosphere in the vehicle cabin.

The vehicle cabin, which serves as a sound field, actually has different acoustic characteristics (also referred to as sound field characteristics, frequency transfer characteristics, or gain characteristics) at different locations therein. For example, there are frequencies that are easier to sense and frequencies that are more difficult to perceive in different passenger positions, e.g., at a driver seat and a rear passenger seat, in the vehicle cabin. It also has been understood that the responses of acoustic characteristics between the speaker position and the passenger position have peaks and dips.

With the conventional sound effect producing apparatus, even if the frequency and sound level of the sound effect radiated from the speaker linearly in proportion to acceleration are increased, since the sound effect as perceived by the ears of the passenger has been processed according to the acoustic characteristics, linearity is lost and some sound effect interruptions tend to occur. Accordingly, the performance level of the conventional sound effect producing apparatus has been somewhat unattractive.

SUMMARY OF THE INVENTION

It is therefore an object of the present invention to provide a mobile object sound effect producing apparatus which is capable of achieving an excellent acoustic effect within a sound field when a sound effect is produced in the sound field, by increasing the linearity of the sound effect and reducing sound effect interruptions, which would otherwise occur due to peaks and dips of the responses of acoustic characteristics of the sound field (also referred to as sound field characteristics), in view of the acoustic characteristics of the sound field.

Another object of the present invention is to provide a mobile object sound effect producing apparatus, which is capable of preventing large sound effects from being produced when the engine on the mobile object is raced, or when the transmission on the mobile object has a throttle kickdown.

According to the present invention, there is provided a mobile object sound effect producing apparatus comprising a waveform data table for storing waveform data in one cyclic period, reference signal generating means for generating a reference signal of harmonics based on an engine rotation frequency by successively reading the waveform data from the waveform data table, acoustic control means for generating a control signal based on the reference signal, and output means for converting the control signal into a sound effect and outputting the sound effect, wherein the acoustic control means has a first acoustic corrector for correcting the reference signal depending on the engine rotation frequency to generate the control signal, the first acoustic corrector having gain characteristics represented by an inversion of gain characteristics which change depending on the frequency of the reference signal from the output means to a passenger position.

With the above arrangement, the reference signal is corrected according to gain characteristics represented by an inversion of gain characteristics (vehicle cabin acoustic characteristics), which change depending on the frequency of the reference signal from the output means to the passenger position, and converted as a sound effect from the output means into a vehicle cabin. Consequently, the sound effect output from the output means is prevented from changing depending on the frequency at the ears of a passenger in the passenger position. Therefore, flat gain vs. frequency characteristics are available at the passenger position. The sound effect generated at the passenger position is thus made linear depending on the engine rotational speed, or stated otherwise, depending on the state of the noise source.

The acoustic control means also has a second acoustic corrector for adjusting the magnitude of the reference signal within a predetermined frequency range, wherein the first acoustic corrector and the second acoustic corrector correct the reference signal depending on the engine rotation frequency to generate the control signal.

Consequently, the second acoustic corrector for adjusting the magnitude of the reference signal within a predetermined frequency range can adjust the amplitude of the reference signal only within a certain frequency range to emphasize an acoustic signal at desired frequencies at the ears of the passenger, thereby producing a sound effect for a tone color to be staged.

The reference signal generating means has a plurality of reference signal generators for generating respective reference signals of harmonics based on the engine rotation frequency by successively reading the waveform data from the waveform data table, and the acoustic control means further has a plurality of first acoustic correctors having respective gain characteristics represented by an inversion of gain characteristics which change depending on the frequencies of the reference signals from the output means to the passenger position, a plurality of third acoustic correctors for adjusting the magnitudes of the reference signals of the harmonics of respective degrees, and a combiner for combining the reference signals of the harmonics which have been corrected by the first acoustic correctors and the third acoustic correctors and outputting the control signal.

With the above arrangement, the acoustic correctors for adjusting the magnitudes of the reference signals of the harmonics of respective degrees correct the reference signals depending on the degrees thereof for producing a sound effect having a deep tone color to be staged at the ears of the passenger that is present in the passenger position.

The output means comprises a first output unit and a second output unit, and the mobile object sound effect producing apparatus further comprises a compensation filter for processing the control signal according to predetermined characteristics. The first output unit converts the control signal into the sound effect and outputs the sound effect, and the second output unit converts the control signal which has been processed by the compensation filter into a sound effect and outputs the sound effect, wherein the predetermined characteristics of the compensation filter comprise transfer characteristics represented by the product of −1 and the quotient produced when the transfer characteristics of an acoustic signal from the first output unit to another passenger position are divided by the transfer characteristics from the second output unit to the other passenger position.

With the above arrangement, since the compensation filter corrects the control signal according to the transfer characteristics represented by the product of −1 and the quotient produced when the transfer characteristics of an acoustic signal from the first output unit to the other passenger position, e.g., a rear seat in the motor vehicle, are divided by the transfer characteristics from the second output unit to the other passenger position, the sound effect from the first output unit is canceled out by the sound effect from the second output unit at the other passenger position. The sound effect that reaches the other passenger position is reduced, and the vehicle cabin is kept quiet at a given position such as the other passenger position.

The mobile object sound effect producing apparatus further comprises a frequency change detector for determining a frequency change per unit time of the engine rotation frequency, and a sound pressure adjuster for correcting the control signal according to gain characteristics depending on the frequency change, and outputting the corrected control signal to the first output unit, or to the first output unit and the compensation filter, wherein the gain characteristics of the sound pressure adjuster are set to a constant gain when the frequency change is not greater than a predetermined value.

With the above arrangement, a frequency change per unit time of the engine rotation frequency is detected, a sound effect corrected by the sound pressure adjuster having gain characteristics depending on the frequency change is generated, and the gain characteristics are set to a constant gain when the frequency change is not greater than a predetermined value. Therefore, depending on the acceleration of the motor vehicle, the sound pressure level is increased to allow the passenger to feel the acceleration based on the sound effect. Inasmuch as the sound pressure level is constant when the motor vehicle is accelerated at rates not greater than the predetermined value, including small accelerations and decelerations, beat sounds due to small accelerations and decelerations are prevented from occurring while the motor vehicle is cruising at a constant speed.

The gain characteristics of the sound pressure adjuster are set to a gain that decreases as the frequency change increases, when the frequency change is greater than a second predetermined value.

With this setting, at the time the frequency change of the engine rotation frequency increases when the engine is raced or the transmission on the mobile object has a throttle kickdown, the motor vehicle is prevented from being erroneously recognized as being fully accelerated, and a considerably large sound effect is prevented from being generated, so that the passenger in the motor vehicle will not feel strange or uncomfortable. Specifically, when the frequency change increases in excess of a value that represents a fully open throttle position in a first gear position, the gain is reduced as the frequency change increases. Accordingly, no large sound effect is produced.

The mobile object sound effect producing apparatus further comprises a frequency change detector for determining a frequency change per unit time of the engine rotation frequency, and a sound pressure adjuster for correcting the control signal according to gain characteristics depending on the frequency change, and outputting the corrected control signal to the first output unit, or to the first output unit and the compensation filter, wherein the gain characteristics of the sound pressure adjuster are set to a gain which decreases as the frequency change increases when the frequency change is greater than a second predetermined value.

With the above setting, at the time the frequency change of the engine rotation frequency increases when the engine is raced or the transmission on the mobile object has a throttle kickdown, the motor vehicle is prevented from being erroneously recognized as being fully accelerated, and a considerably large sound effect is prevented from being generated, so that the passenger in the motor vehicle will not feel strange or uncomfortable. Specifically, when the frequency change increases in excess of a value that represents a fully open throttle position in a first gear position, the gain is reduced as the frequency change increases. Accordingly, no large sound effect is produced.

In all of the above features, according to the present invention an open-loop control system is employed, rather than a feedback control system in which the sound effect from the output means is detected by an input means (sound detecting means) such as a microphone or the like and fed back to a component. Consequently, the mobile object sound effect producing apparatus has good circuit stability, can be developed in a shortened period of time, and can be reduced in cost.

According to the present invention, when a sound effect is generated, the linearity of the sound effect is increased and sound effect interruptions are reduced which would otherwise occur due to peaks and dips of the responses of acoustic characteristics of the sound field (also referred to as sound field characteristics), in view of the acoustic characteristics of the sound field.

Furthermore, the magnitude of the sound effect in a predetermined frequency range can be adjusted.

In addition, a sound effect of multiple degrees depending on the fuel combustion in the engine of the motor vehicle can be generated.

Moreover, a sound effect can be generated at one passenger position, and a sound effect can be eliminated to achieve a quiet state at another passenger position.

A sound effect can be generated depending on the accelerating action on the accelerator pedal and the transmission on the motor vehicle, and the generation of a sound effect can be suppressed when the motor vehicle is accelerated at rates not greater than a predetermined value, including decelerations.

Since a large sound effect is prevented from being generated when the engine is raced or the transmission on the mobile object has a throttle kickdown while the motor vehicle is traveling, the passenger in the motor vehicle will not feel strange and uncomfortable.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
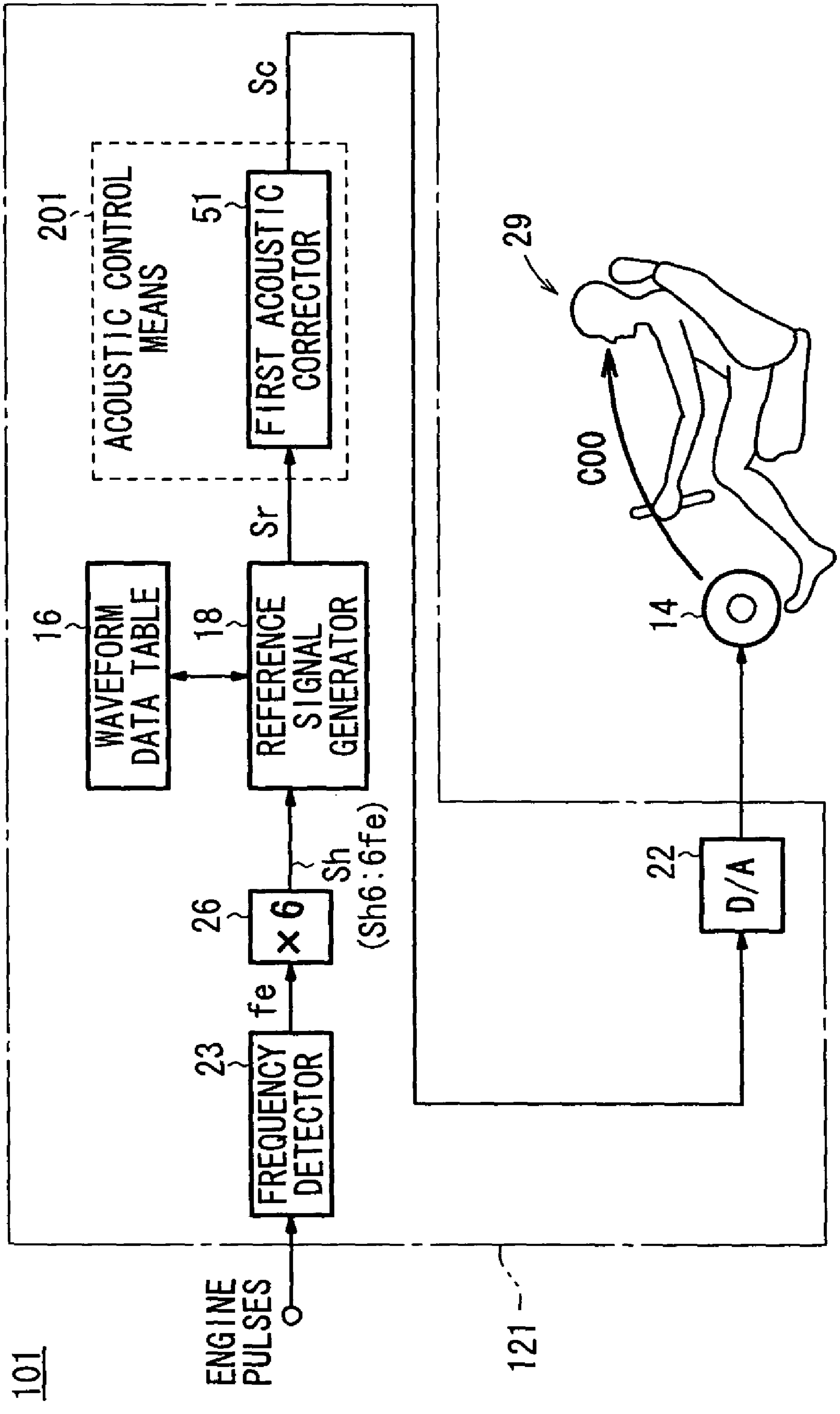
FIG. 1 is a block diagram of a mobile object sound effect producing apparatus according to a first embodiment of the present invention.

The mobile object sound effect producing apparatus according to preferred embodiments of the present invention shall be described below with reference to the drawings.

Like or corresponding parts of the apparatus are denoted by like or corresponding reference characters.

FIG. 1 shows in block form a mobile object sound effect producing apparatus 101 according to a first embodiment of the present invention.

The mobile object sound effect producing apparatus 101 comprises an ECU (Electronic Control Unit) 121 serving as a general control means, and a speaker 14 serving as an output means.

The ECU 121 is mounted in the dashboard of a motor vehicle, and essentially includes a waveform data table 16 for storing waveform data in one cyclic period, a reference signal generator 18 serving as a reference signal generating means for generating a reference signal Sr which has a harmonic (harmonic signal) Sh based on an engine rotation frequency fe of the motor vehicle by successively reading waveform data from the waveform data table 16, and an acoustic control means 201 for generating a control signal Sc based on the reference signal Sr.

The speaker 14 serves to apply sounds to a passenger in a passenger position 29 such as a driver seat or a front passenger seat. The speaker 14 is fixedly disposed on a panel in each of front doors on opposite sides of the motor vehicle, or on each of kick panels on opposite sides of the motor vehicle, i.e., door-side inner panel surfaces alongside of a driver leg space. The speaker 14 may alternatively be disposed beneath the center of the dashboard.

The speaker 14 transduces a control signal Sc that is output from the acoustic control means 201 of the ECU 121 through a D/A converter 22 into a sound effect in the form of an acoustic signal, and outputs the sound effect. An output amplifier (not shown) is connected between the D/A converter 22 and the speaker 14, wherein a gain thereof may be varied by the passenger.

The reference signal generator 18 has an input port connected to a series-connected circuit comprising a frequency detector 23 such as a frequency counter or the like for detecting the frequency of engine pulses which are produced by a Hall-effect device or the like when the output shaft of the engine mounted on the motor vehicle rotates, and a multiplier 26 serving as a multiplying means for outputting a harmonic signal Sh6 which has a frequency (sixth harmonic frequency) 6*fe* that is six times an engine pulse frequency fe (fundamental frequency) detected by the frequency detector 23. The multiplier 26 multiplies the engine pulse frequency fe by an integer such as 2, 3, 4, 5, 6, . . . or a real number such as 2.5, 3.3, . . . .

Between the speaker 14 and the passenger position (front-seat passenger position) 29, inherent acoustic characteristics (sound-field characteristics, frequency transfer characteristics, or sound-field gain characteristics) C00 are produced due to the passenger cabin structure of the motor vehicle, the materials used in the passenger cabin of the motor vehicle, etc. Such gain characteristics C00 have complex disturbances such as peaks and dips in the responses thereof because of the passenger cabin structure, the materials used, etc.

The sound-field gain characteristics C00 are obtained as gain frequency characteristics (hereinafter simply referred to as gain characteristics or frequency characteristics) representing the ratio of the amplitude (magnitude) to frequency of a signal that is output from a microphone which serves as a sound detecting means disposed in the front seat passenger position 29, or specifically at the position of an ear of the passenger in the front seat passenger position 29, when the frequency of a sine-wave signal having a constant amplitude that is applied to the speaker 14 is continuously changed from lower to higher frequencies. The frequency of the sine-wave signal, which is referred to above, is not the engine pulse frequency, but the frequency of an acoustic signal.

Stated otherwise, the sound-field gain characteristics C00 represent gain characteristics obtained at the front seat passenger position 29 when the reference signal generator 18 and the D/A converter 22 are directly connected to each other, without the acoustic control means 201 interposed therebetween, and the frequency of a sine-wave signal having a constant amplitude that is generated by the reference signal generator 18 is continuously changed from a lower frequency such as several tens [Hz] to a higher frequency such as 1 [kHz]. The gain represented by the gain characteristics C00 changes depending on the frequency of the reference signal Sr from the speaker 14 to the front seat passenger position 29. More strictly, the gain represented by the gain characteristics C00 changes depending on the frequency of the reference signal Sr from the reference signal generator 18 to the front seat passenger position 29.

Figure 2A:
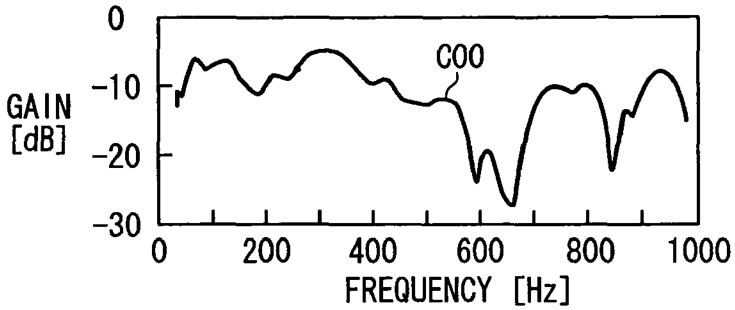
FIG. 2A is a diagram showing a measured gain characteristic curve.

FIG. 2A shows a gain characteristic curve C00, actually measured in a frequency range from about 30 [Hz] to about 970 [Hz], which represents sound-field characteristics from the position of the speaker 14 to the front seat passenger position 29, or more exactly to the ears of the passenger. The horizontal axis of FIG. 2A represents frequency [Hz] and the vertical axis gain [dB].

The reference signal Sr is generated by means of the waveform data table 16 and is stored in a memory.

Figures 3A, 3B:
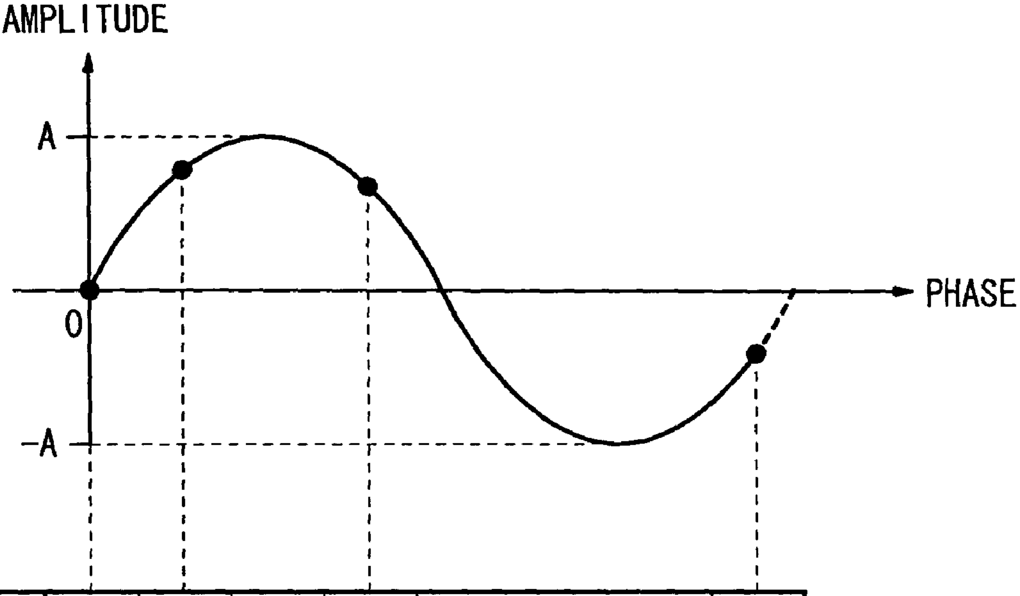
FIG. 3A is a diagram showing waveform data stored in a waveform data table in the mobile object sound effect producing apparatus.
FIG. 3B is a diagram showing a sine wave, which is generated by referring to the waveform data memory.

As schematically shown in FIGS. 3A and 3B, the waveform data table 16 comprises instantaneous value data stored as waveform data at respective addresses, the instantaneous value data representing a predetermined number (N) of instantaneous values into which the waveform of a sine wave in one cyclic period is divided at equal intervals along a time axis (=phase axis). The addresses (i) are indicated by integers (i=0, 1, 2, . . . , N−1) ranging from 0 to (the predetermine number −1). An amplitude value A shown in FIGS. 3A and 3B is represented by 1 or any desired positive real number. Therefore, the waveform data at the address i is calculated as Asin(360°×i/N). Stated otherwise, one cycle of a sine waveform is divided into N sampled values at sampling points spaced over time, and data generated by quantizing the instantaneous values of the sine wave at the respective sampling points are stored in the memory as waveform data at respective addresses, which are represented by the respective sampling points.

The reference signal generator 18 generates a reference signal Sr, which comprises a sine-wave signal having a frequency corresponding to the frequency of the harmonic signal Sh6, when it reads the waveform data from the waveform data table 16 while changing the readout address period depending on the period of the harmonic signal Sh that is applied to the reference signal generator 18.

Figure 2B:
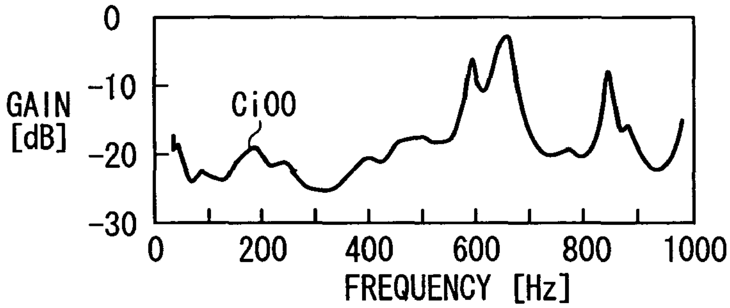
FIG. 2B is a diagram showing a gain characteristic curve, which is an inversion of the measured gain characteristic curve.

The acoustic control means 201 has a first acoustic corrector 51. The first acoustic corrector 51 functions as a filter whose gain characteristics (having a horizontal axis representing frequency and a vertical axis representing gain) are represented by the gain characteristic curve (inverted gain characteristic curve) Ci00 shown in FIG. 2B, which is an inversion of the gain characteristic curve C00 shown in FIG. 2A, and which changes depending on the frequency of the reference signal Sr from the speaker 14 to the front seat passenger position 29.

The inverted gain characteristic curve Ci00 is represented by a gain characteristic curve having an increased gain level at frequencies where acoustically less transmissive dips are present in the gain characteristic curve C00 shown in FIG. 2A, and having a reduced gain level at frequencies where acoustically more transmissive peaks are present in the gain characteristic curve C00 shown in FIG. 2A. The inverted gain characteristic curve Ci00 is expressed by an equation (transfer function) as Ci00=B/C00 where B represents a reference value.

The mobile object sound effect producing apparatus 101 according to the first embodiment of the present invention operates as follows. When the reference signal generator 18 generates a reference signal Sr having a constant amplitude in a frequency range from 30 [Hz] to 970 [Hz], the corrective gain characteristic curve Ci00 of the first acoustic corrector 51 and the sound-field gain characteristic curve C00 are multiplied at the front seat passenger position 29, producing gain characteristics C1 according to which sounds having a flat sound pressure level in the frequency range are heard at the front seat passenger position 29, as indicated by the gain characteristic curve C1 in FIG. 2C.

Therefore, when the cyclic period of the engine pulses changes or remains constant as the passenger accelerates or decelerates the motor vehicle, or keeps the motor vehicle running at a constant speed, the reference signal generator 18 generates a sine-wave reference signal Sr whose frequency increases, decreases, or remains constant substantially in real time, depending on the harmonic signal Sh6 having a sixth-harmonic frequency 6*fe* produced by the multiplier 26 from the engine rotation frequency fe that is detected by the frequency detector 23.

The reference signal Sr is converted by the acoustic control means 201 into a control signal Sc that has been corrected by the gain characteristic curve Ci00 of the first acoustic corrector 51. Consequently, the sound effect output from the speaker 14 is prevented from changing depending on the frequency at the front seat passenger position 29 due to the vehicle cabin acoustic characteristics C00. Therefore, flat gain vs. frequency characteristics are available at the front seat passenger position 29. The sound effect generated at the front seat passenger position 29 is thus made linear depending on the engine rotational speed (six times the engine rotation frequency fe), or stated otherwise, depending on the state of the noise source.

Figure 4:
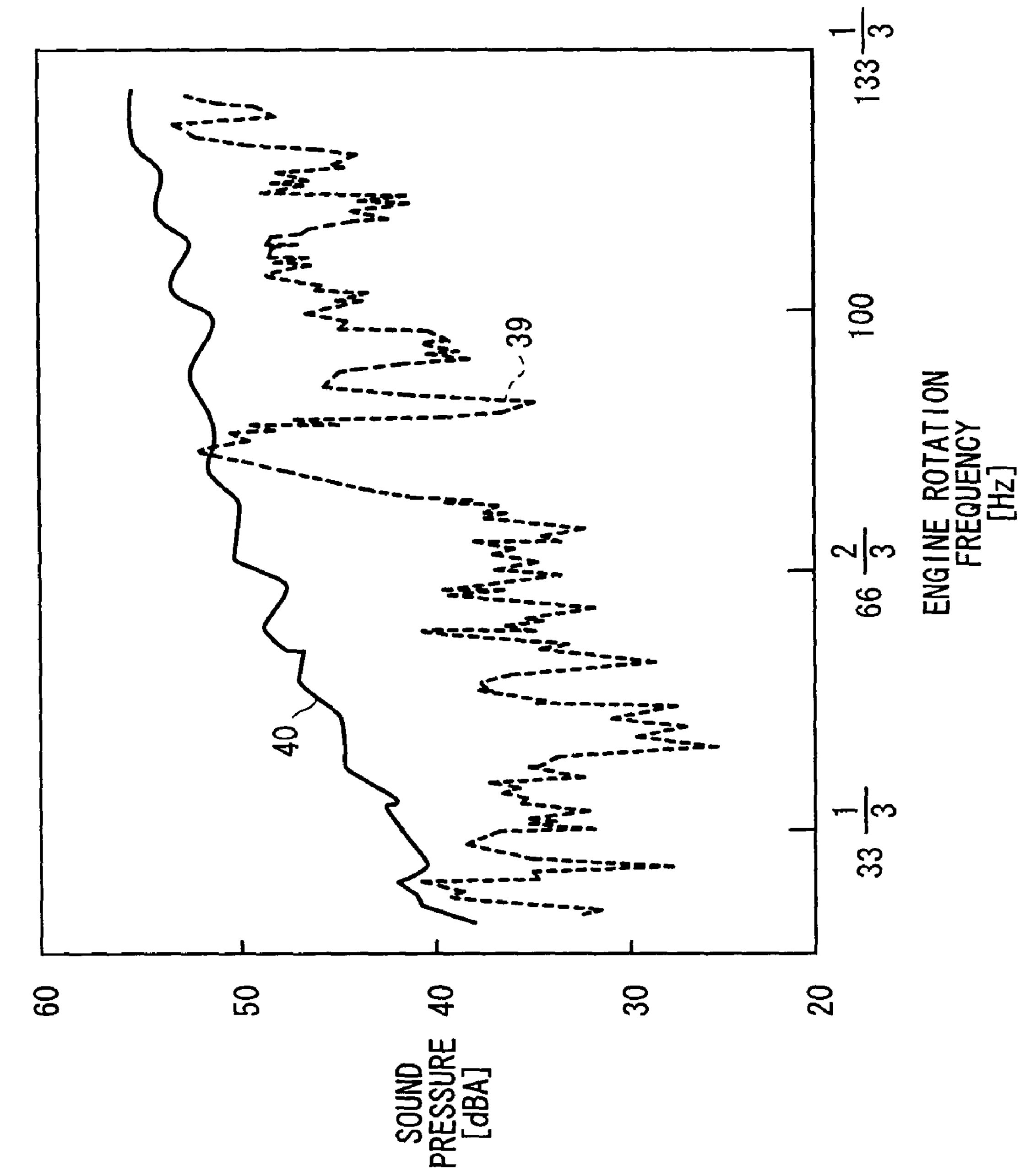
FIG. 4 is a diagram showing frequency characteristics of sound pressure levels before and after they are corrected.

FIG. 4 shows frequency characteristics of sound pressure levels at the front seat passenger position 29 before and after they are corrected. To make the sound effect more linear in achieving the frequency characteristics shown in FIG. 4, the reference signal Sr or the control signal Sc is generated so as to have its amplitude increase in proportion to the engine rotation frequency fe.

As shown in FIG. 4, a corrected characteristic curve 40 has a sound pressure level that changes more linearly depending on the engine rotation frequency fe than the uncorrected characteristic curve 39, which has dips and peaks.

The process referred to above for generating at the front seat passenger position 29 the sound effect which changes linearly as the engine rotation frequency fe increases or the motor vehicle is accelerated according to the first embodiment shall be referred to as a sound field adjusting process or a flattening process.

Figure 5:
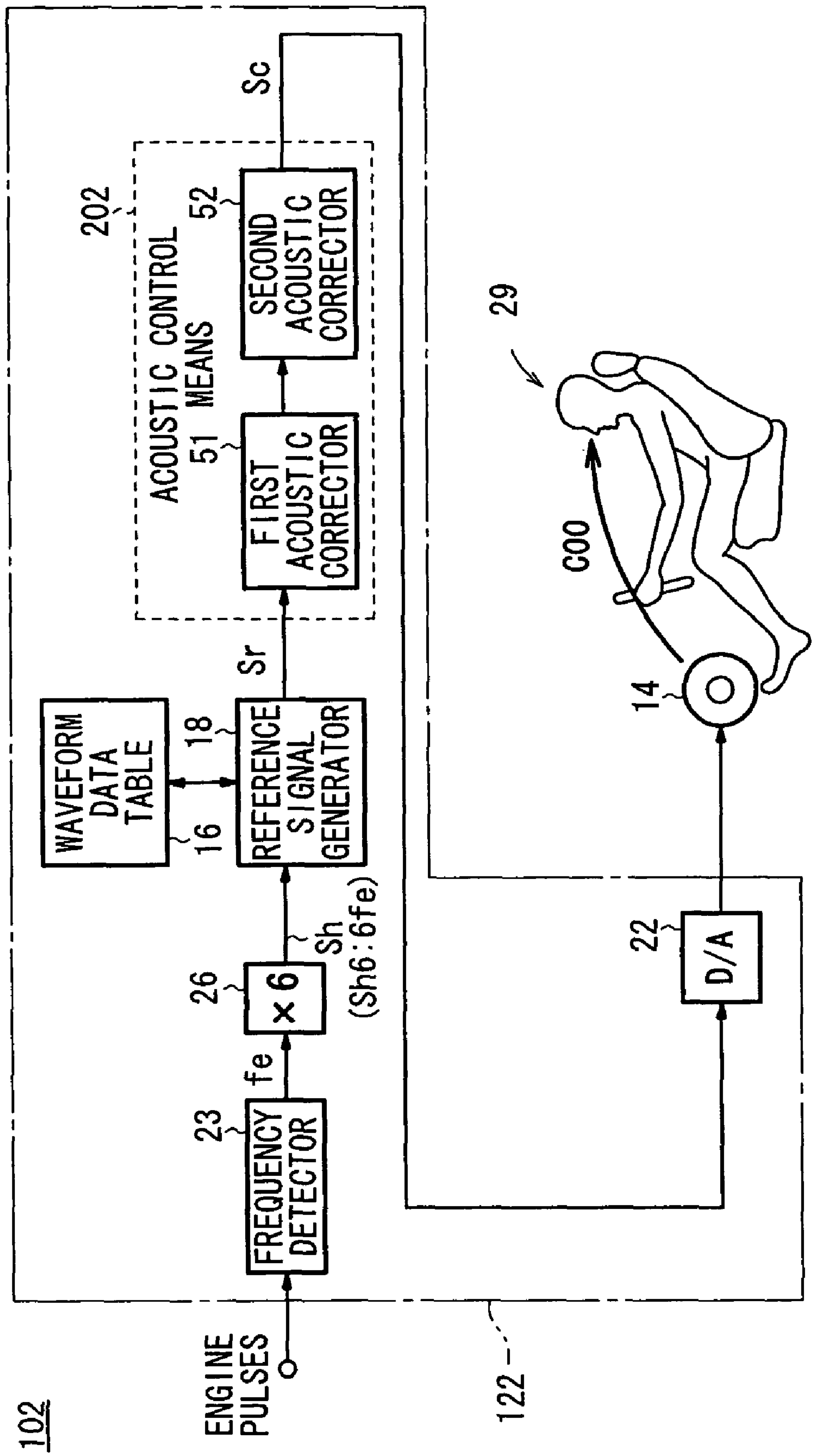
FIG. 5 is a block diagram of a mobile object sound effect producing apparatus according to a second embodiment of the present invention.

FIG. 5 shows in block form a mobile object sound effect producing apparatus 102 according to a second embodiment of the present invention. As shown in FIG. 5, the mobile object sound effect producing apparatus 102 comprises an ECU 122 and the speaker 14.

The mobile object sound effect producing apparatus 102 according to the second embodiment differs from the mobile object sound effect producing apparatus 101 according to the first embodiment in that an acoustic control means 201 comprises the first acoustic corrector 51 and a second acoustic corrector 52.

The second acoustic corrector 52 comprises a filter or an amplifier functioning as an equalizer for adjusting the amplitude of the reference signal Sr within a certain frequency range.

Figure 2C:
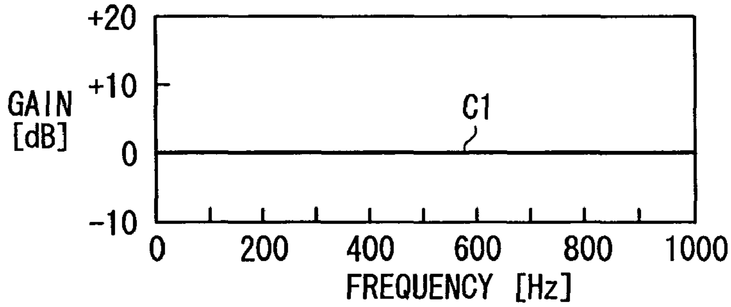
FIG. 2C is a diagram showing a corrected gain characteristic curve.
Figure 2D:
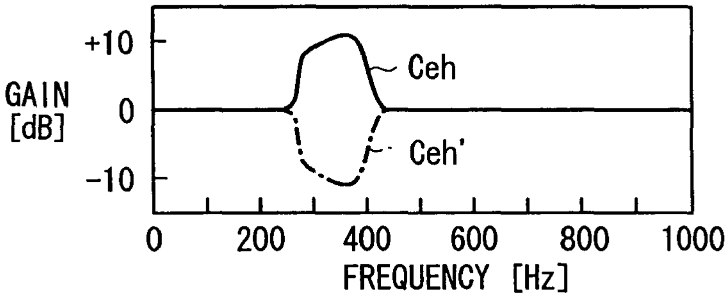
FIG. 2D is a diagram showing a gain characteristic curve with enhanced gains in a certain frequency range.
Figure 2E:
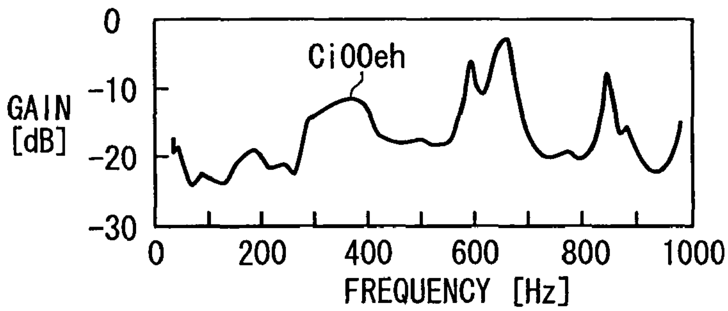
FIG. 2E is a diagram showing the inverted gain characteristic curve with enhanced gains in the certain frequency range.

For example, as indicated by the solid-line curve in FIG. 2D, the second acoustic corrector 52 provides gain characteristics represented by a gain characteristic curve Ceh having increased gains in a frequency range from 300 [Hz] to 450 [Hz], for example. Therefore, the first acoustic corrector 51 and the second acoustic corrector 52 provide a joint gain characteristic curve Ci00*eh* as shown in FIG. 2E. The joint gain characteristic curve Ci00*eh* shown in FIG. 2E has higher gains, i.e., produces higher sound pressure levels, in the frequency range from 300 [Hz] to 450 [Hz] than the inverted gain characteristic curve Ci00 shown in FIG. 2B.

The mobile object sound effect producing apparatus 102 according to the second embodiment provides the gain characteristic curve Ceh indicated by the solid line in FIG. 2D at the front seat passenger position 29. The second acoustic corrector 52 may provide a gain characteristic curve Ceh' indicated by the dotted line in FIG. 2E at the front seat passenger position 29, for thereby reducing gains or lowering sound pressure levels within the above frequency range.

Consequently, the second acoustic corrector 52 can adjust the amplitude of the reference signal Sr only in a certain frequency range to emphasize an acoustic signal only at desired frequencies at the front seat passenger position 29, thereby producing a sound effect for a tone color to be staged. The process referred to above for emphasizing an acoustic signal only at desired frequencies according to the second embodiment shall be referred to as a frequency emphasizing process.

Figure 6:
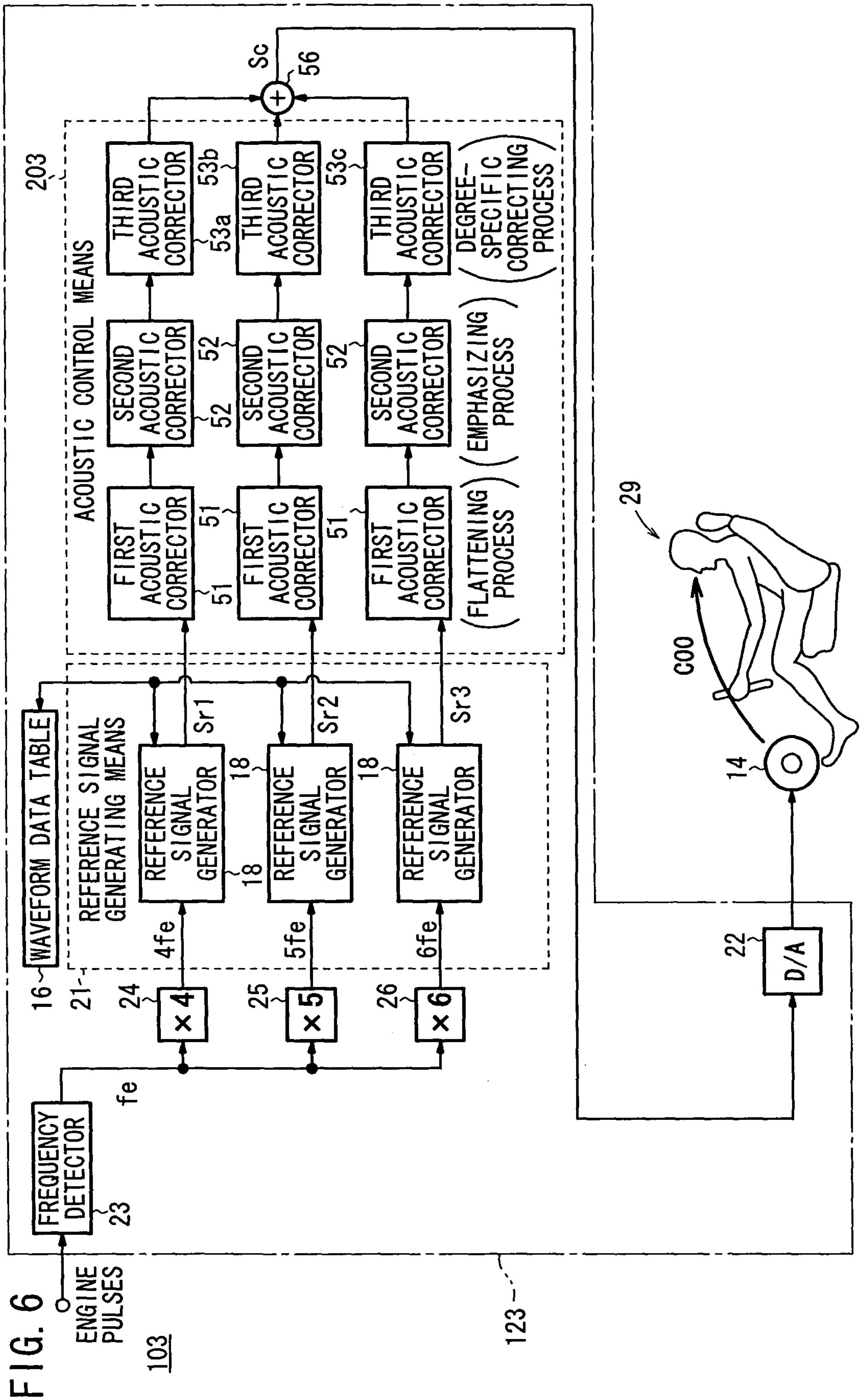
FIG. 6 is a block diagram of a mobile object sound effect producing apparatus according to a third embodiment of the present invention.

FIG. 6 shows in block form a mobile object sound effect producing apparatus 103 according to a third embodiment of the present invention. As shown in FIG. 6, the mobile object sound effect producing apparatus 103 comprises an ECU 123 and the speaker 14.

The ECU 123 includes multipliers 24, 25, 26 for converting the engine rotation frequency fe detected by the frequency detector 23 respectively into a frequency 4*fe* (fourth harmonic frequency), a frequency 5*fe* (fifth harmonic frequency), and a frequency 6*fe* (sixth harmonic frequency), which are four, five, and six times, respectively, the engine rotation frequency fe.

The ECU 123 also includes a reference signal generating means 21 comprising three reference signal generators 18, which are identical to each other.

The reference signal generators 18 generate respective reference signals Sr1, Sr2, Sr3 based on the engine rotation frequency fe by reading waveform data from the waveform data table 16.

The ECU 123 further includes an acoustic control means 203. The acoustic control means 203 comprises three first acoustic correctors 51 which are identical to each other and have respective gain characteristics Ci00 which are an inversion of the gain characteristics C00 that change depending on the frequencies of the reference signals Sr1, Sr2, Sr3 from the speaker 14 to the front seat passenger position 29, three second acoustic correctors 52 which are identical to each other for emphasizing the reference signals Sr1, Sr2, Sr3 within predetermined frequency ranges, and three third acoustic correctors 53*a*, 53*b*, 53*c* which are different from each other, i.e., having different frequency characteristics, for adjusting the respective amplitudes of the reference signals Sr1, Sr2, Sr3 with respect to respective degrees (4, 5, 6 in the embodiment) of the three harmonic signals. Three signals that are produced by the acoustic control means 203 when the acoustic control means 203 corrects the reference signals Sr1, Sr2, Sr3 are combined into a control signal Sc by a combiner 56.

As described above, the mobile object sound effect producing apparatus 103 according to the third embodiment has the three third acoustic correctors 53*a*, 53*b*, 53*c* having different frequency characteristics for adjusting the respective amplitudes of the reference signals Sr1, Sr2, Sr3 with respect to respective degrees of the harmonic signals. When the third acoustic correctors 53*a*, 53*b*, 53*c* correct the reference signals Sr1, Sr2, Sr3 based on the respective degrees of the harmonic signals, a sound effect having a deep tone color to be staged is generated at the ears of the passenger who is present in the front seat passenger position 29. Therefore, the mobile object sound effect producing apparatus 103 has an attractive performance level. The process referred to above for correcting each reference signal depending on the degree of the corresponding harmonic signal shall be referred to as a degree-specific correcting process.

Figure 7:
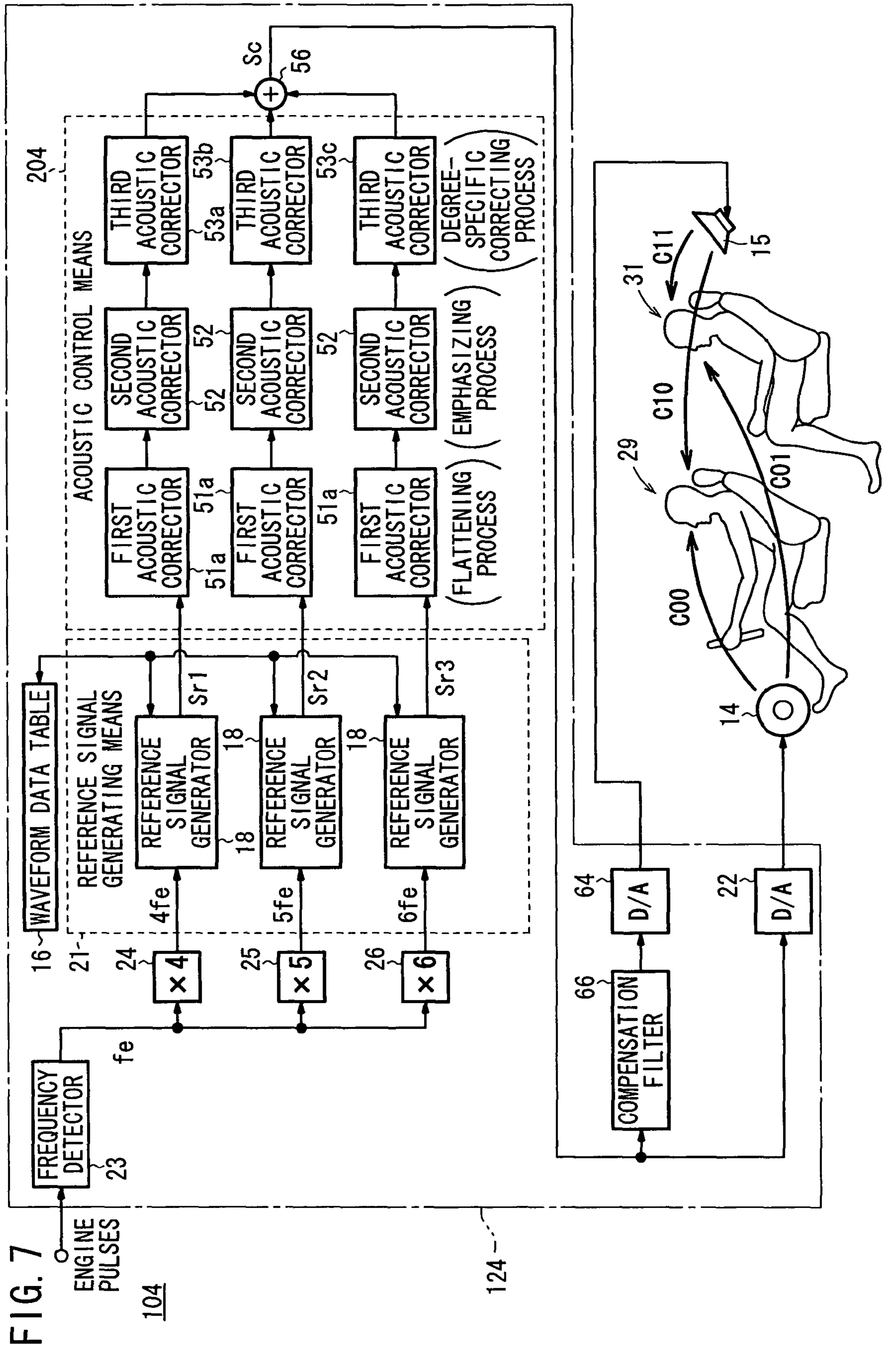
FIG. 7 is a block diagram of a mobile object sound effect producing apparatus according to a fourth embodiment of the present invention.

FIG. 7 shows in block form a mobile object sound effect producing apparatus 104 according to a fourth embodiment of the present invention. As shown in FIG. 7, the mobile object sound effect producing apparatus 104 comprises an ECU 124, the speaker 14, and a speaker 15.

The speakers 14, 15 are positioned respectively in front and rear positions in the vehicle cabin. At the front seat passenger position 29 on a front seat, the sound effects produced by the front and rear speakers 14, 15 are processed according to a sound field adjusting process or a flattening process so that they are made linear in proportion to acceleration. At a passenger position 31 on a rear seat, the sound effects produced by the front and rear speakers 14, 15 are processed so as to be reduced according to a rear seat compensating process. To perform the rear seat compensating process, the mobile object sound effect producing apparatus 104 includes a compensation filter 66 connected between the output terminal of the combiner 56 and the input terminal of a D/A converter 64 for supplying an analog acoustic signal to the rear speaker 15. The front speaker 14 is mounted on each of the front doors on opposite sides of the motor vehicle, and the rear speaker 15 is mounted on each of the rear doors on opposite sides of the motor vehicle. An output amplifier (not shown) is connected between the D/A converter 64 and the speaker 15, and has a gain that may be varied by the passenger.

Figure 8:
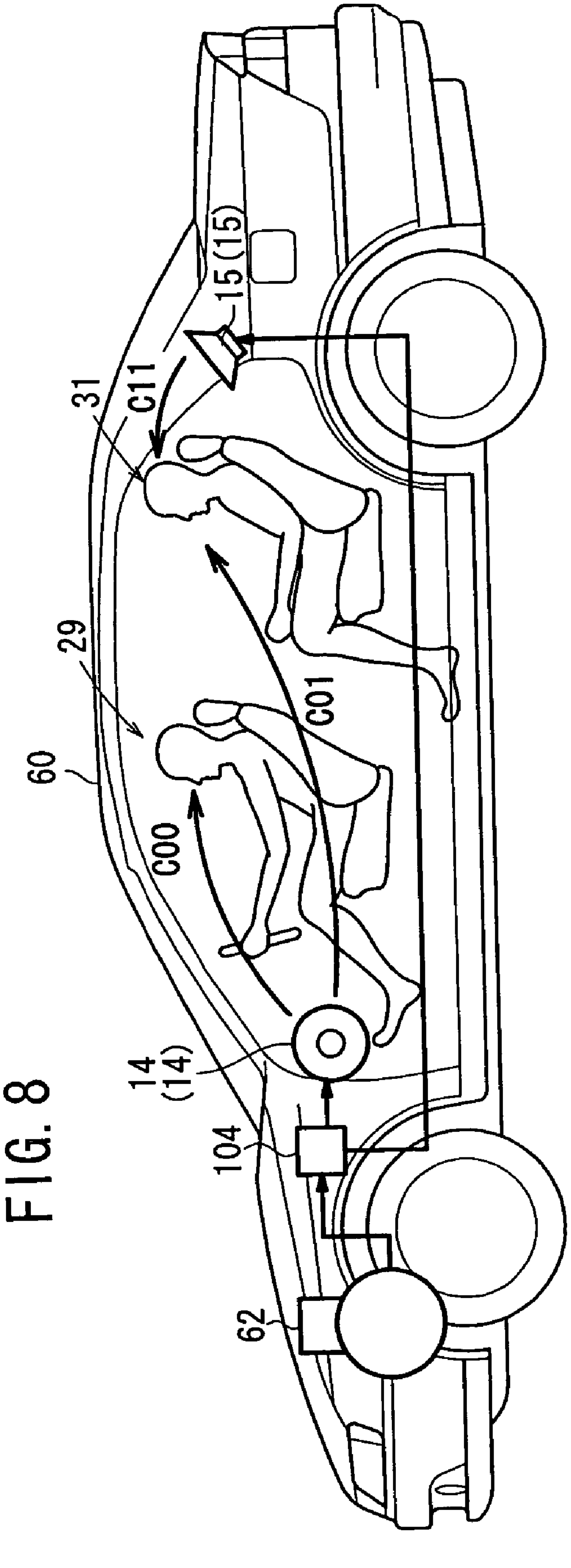
FIG. 8 is a schematic view of a motor vehicle incorporating the mobile object sound effect producing apparatus according to the fourth embodiment into the dashboard.

FIG. 8 schematically shows in side elevation a motor vehicle 60 incorporating the mobile object sound effect producing apparatus 104, which is mounted on the dashboard. The motor vehicle 60 has an engine 62 shown schematically in FIG. 8.

Operation of the mobile object sound effect producing apparatus 104 during the rear seat compensating process shall be described below.

Figure 9:
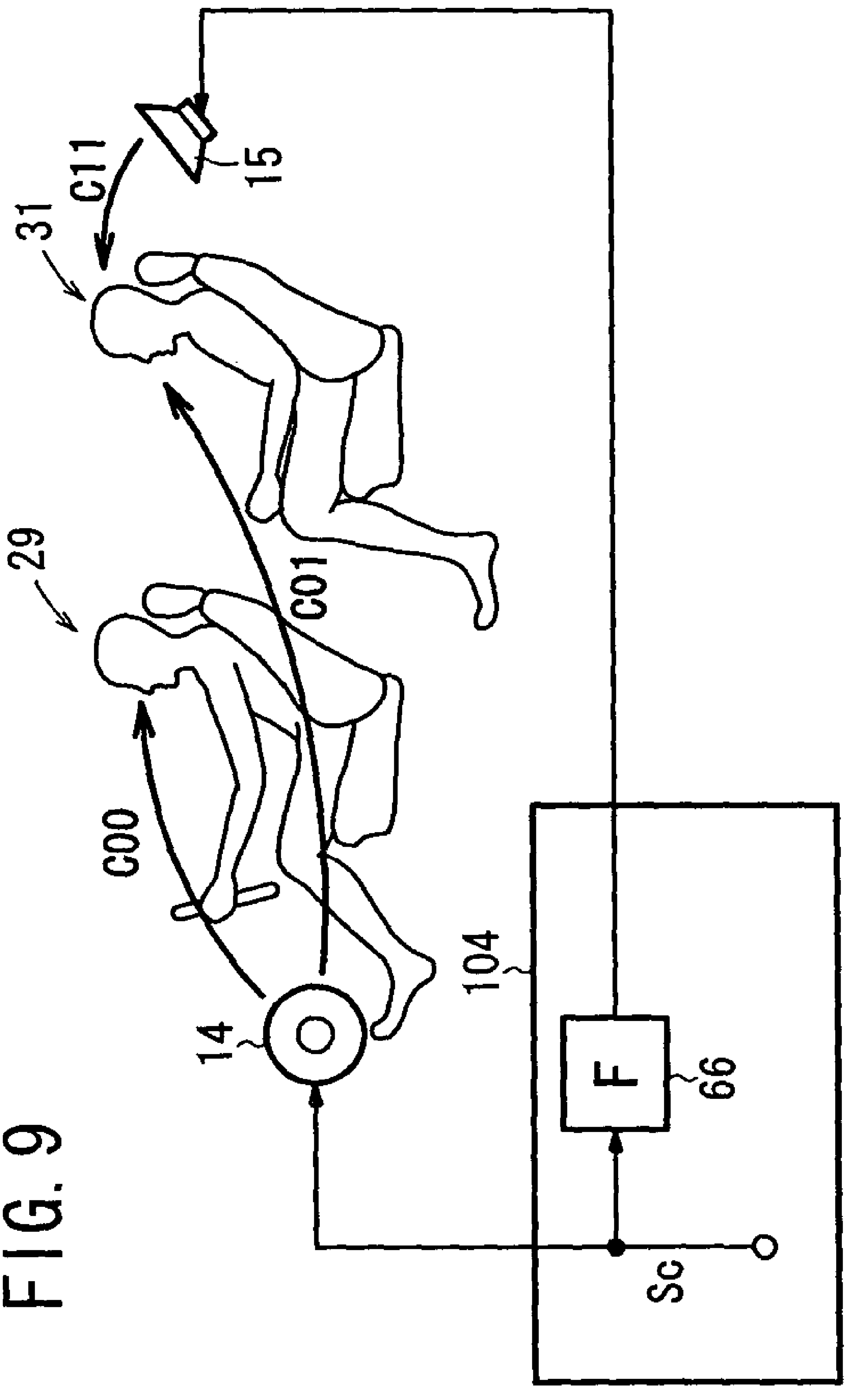
FIG. 9 is a schematic view illustrating the manner in which the mobile object sound effect producing apparatus according to the fourth embodiment operates in a rear seat compensating process.

FIG. 9 illustrates the manner in which the mobile object sound effect producing apparatus 104 operates during the rear seat compensating process.

In FIG. 9, acoustic transfer characteristics, which are measured in advance from the front speaker 14 to the rear seat passenger position 31, are represented by C01, and acoustic transfer characteristics, which are measured in advance from the rear speaker 15 to the rear seat passenger position 31, are represented by C11.

Compensating characteristics (transfer characteristics) F of the compensating filter 66 may be set such that the magnitude of sound at the rear seat passenger position 31 is zero.

At the rear seat passenger position 31, equation (1) shown below may be satisfied. The compensating characteristics F are expressed by equation (2) shown below, which is derived by solving the equation (1) for F.

$$Sc \cdot C01 + Sc \cdot F \cdot C11 = 0 \quad (1)$$

$$F = -(C01/C11) \quad (2)$$

Figure 10:
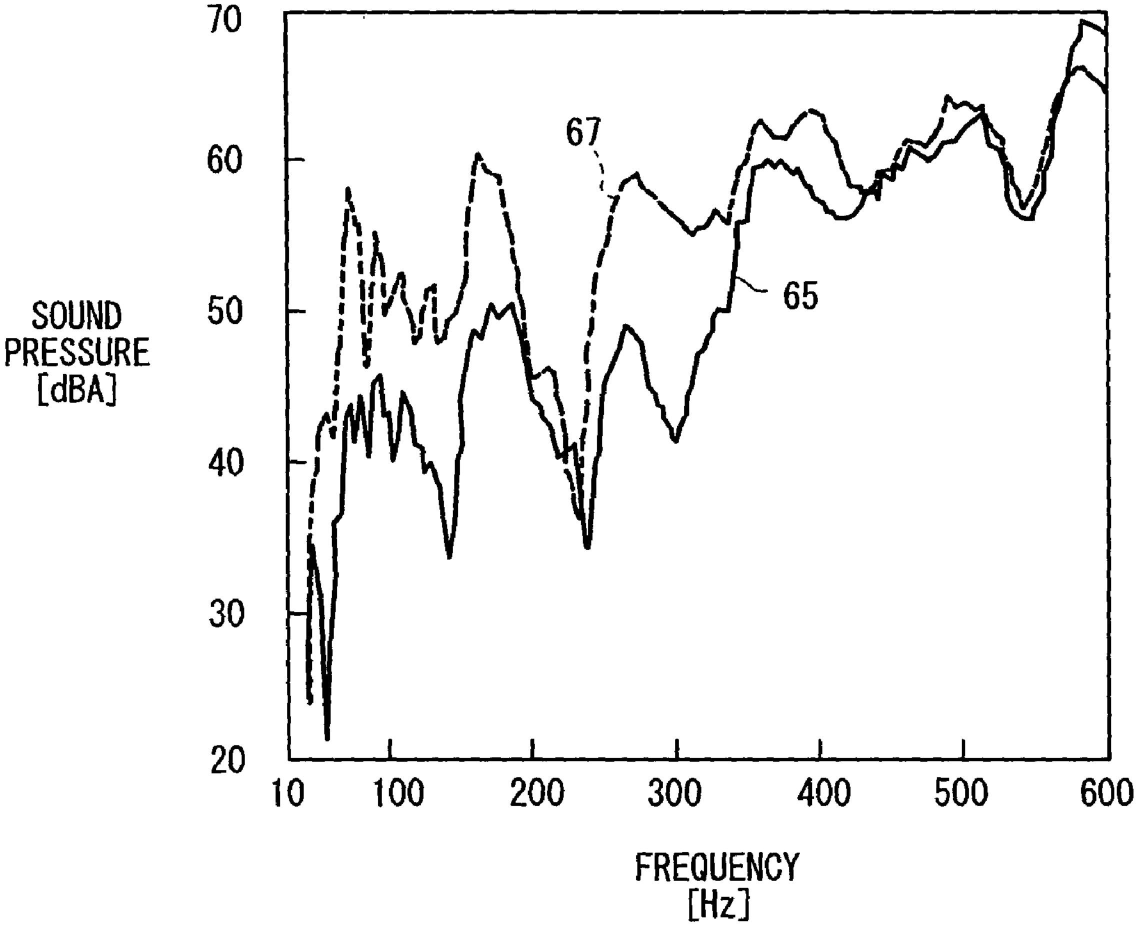
FIG. 10 is a diagram showing measured sound pressure levels at the position of a passenger on a rear seat before and after the rear seat compensating process.

FIG. 10 shows measured sound pressure levels [dB] at the rear seat passenger position 31 before and after the rear seat compensating process is performed by the mobile object sound effect producing apparatus 104 with the compensation filter 66. In FIG. 10, the horizontal axis represents frequency [Hz] and the vertical axis sound pressure level [dBA]. A compensated characteristic curve 65 indicated by the solid line indicates the sound pressure levels produced after the rear seat compensating process is performed, and a compensation-free characteristic curve 67, shown by the broken lines, indicates sound pressure levels produced before the rear seat compensating process is performed. It can be seen from FIG. 10 that the sound pressure levels of the compensated characteristic curve 65 within a frequency range from 50 [Hz] to 350 [Hz], which is a target compensation range, are lower than the sound pressure levels of the compensation-free characteristic curve 67 by about 10 [dBA].

According to the rear seat compensating process, the compensation filter 66 corrects the control signal Sc according to the transfer characteristics F=−(C01/C11) which is represented by the product of −1 and a quotient produced when the acoustic signal transfer characteristics C01 from the speaker 14, as a first output unit to the other passenger position, i.e., the rear seat passenger position 31, are divided by the acoustic signal transfer characteristics C11 from the speaker 15, as a second output unit to the rear seat passenger position 31. Since the sound effect from the speaker 14 is canceled out by the sound effect from the speaker 15 at the rear seat passenger position 31, the sound effect that reaches the rear seat passenger position 31 is reduced. Therefore, the vehicle cabin is kept quiet at a given position such as the rear seat passenger position 31.

A flattening process performed by the mobile object sound effect producing apparatus 104 according to the fourth embodiment shall be described below with reference to FIG. 11.

Figure 11:
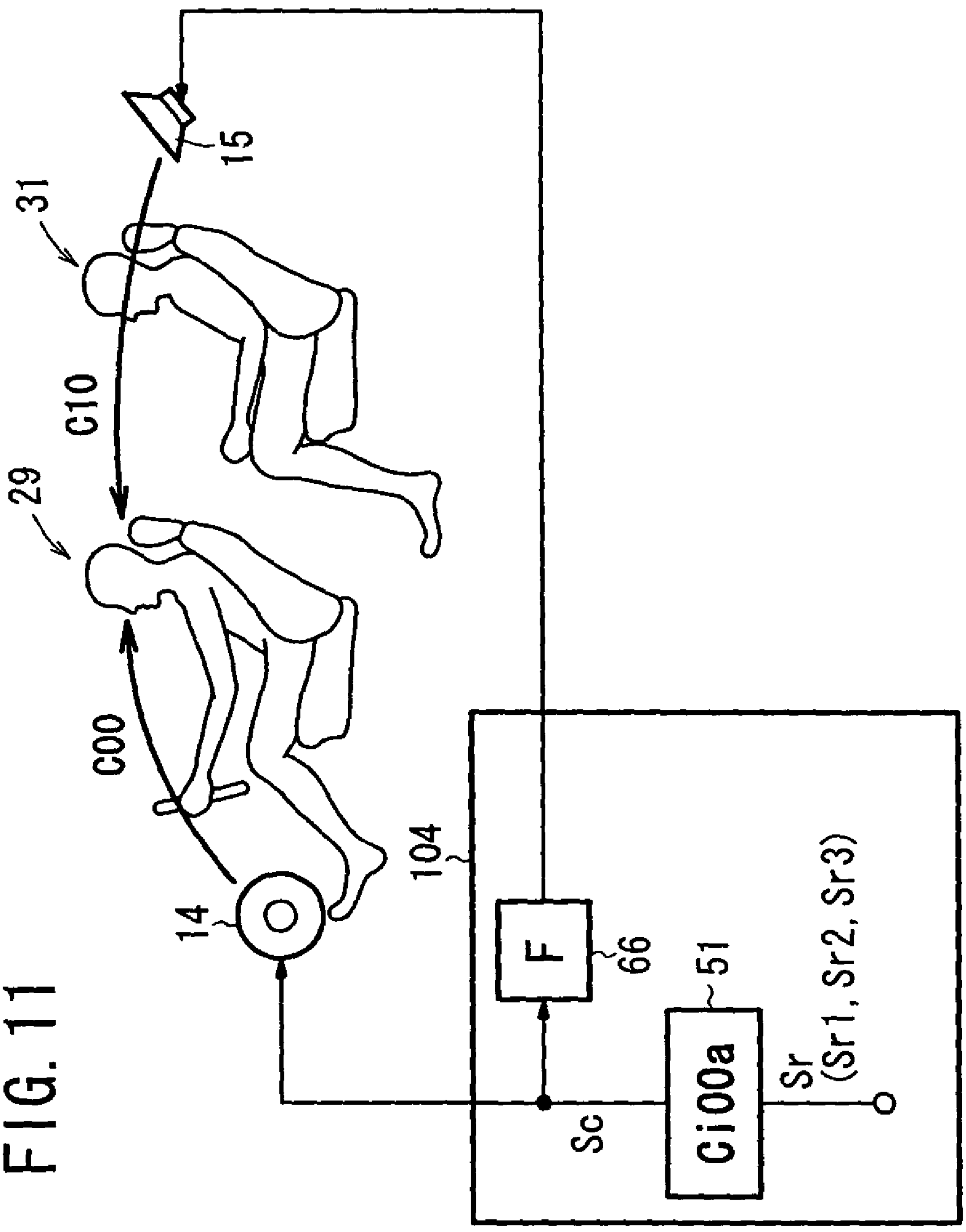
FIG. 11 is a schematic view illustrating the manner in which the mobile object sound effect producing apparatus according to the fourth embodiment operates in a flattening process.

With the rear speaker 15 being provided, as shown in FIG. 11, the total transfer characteristics from the speakers 14, 15 to the front seat passenger position 29 are expressed by the following equation (3):

$$C00 + F \cdot C10 \quad (3)$$

The transfer characteristics expressed by equation (3) can be measured and contain peaks and dips, as with the characteristics shown in FIG. 2A.

When the reference signal Sr has an amplitude which is constant or which increases linearly (uniformly) independently of frequency, it is desirable that the sound level at the front seat passenger position 29 should similarly be of an amplitude which is constant or which increases linearly (uniformly) independently of frequency. Since the magnitude of the sound level at the front seat passenger position 29 is expressed by Sc·(C00+F·C10), if the magnitude of the sound level at the front seat passenger position 29 is to be of a constant magnitude (flat) independent of frequency, then characteristics Ci100*a*={1/(C00+F·C10)}, which are an inversion of the characteristics according to equation (3), may be set in three first acoustic correctors 51*a* (see FIG. 7).

With the characteristics Ci100*a* being thus set in the three first acoustic correctors 51*a*, a flat acoustic characteristic curve, which provides a constant sound pressure level independent of frequency, is provided at the front seat passenger position 29, as indicated by the gain characteristic curve C1 shown in FIG. 2C.

The mobile object sound effect producing apparatus 104 according to the fourth embodiment, which performs the rear seat compensating process and the flattening process, allows a linear sporty sound effect to be heard at the front seat passenger position 29, and also keeps the vehicle cabin relatively quiet at the rear seat passenger position 31.

Figure 12:
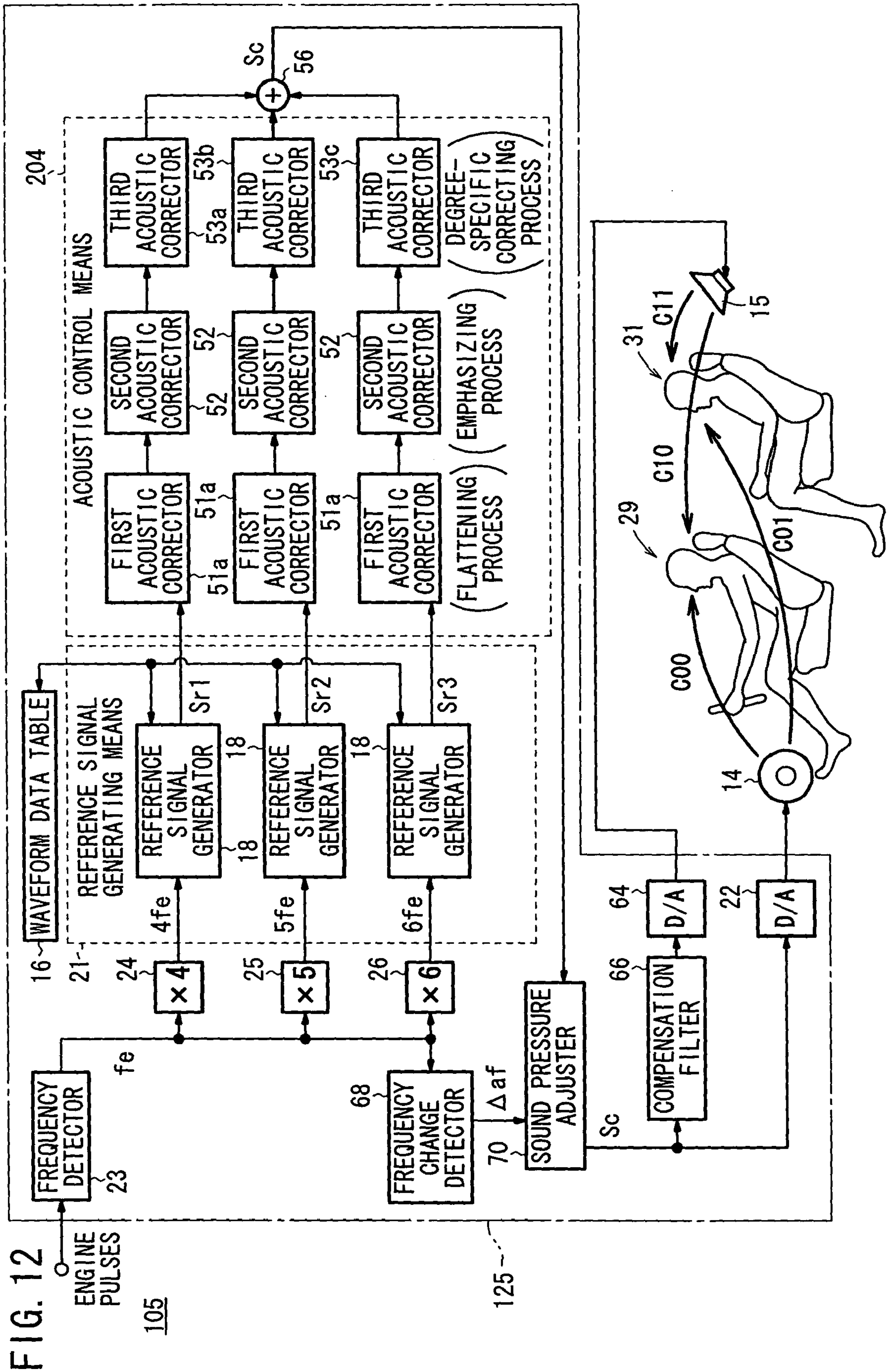
FIG. 12 is a block diagram of a mobile object sound effect producing apparatus according to a fifth embodiment of the present invention.

FIG. 12 shows in block form a mobile object sound effect producing apparatus 105 according to a fifth embodiment of the present invention. As shown in FIG. 12, the mobile object sound effect producing apparatus 105 comprises an ECU 125, and the speakers 14, 15 as output means.

The mobile object sound effect producing apparatus 105 according to the fifth embodiment differs from the mobile object sound effect producing apparatus 104 shown in FIG. 7 in that it additionally has a frequency change detector 68 for determining a frequency change Δaf per unit time of the engine rotation frequency fe, and a sound pressure adjuster 70 having gain characteristics depending on the frequency change Δaf, for correcting the control signal Scc supplied from the combiner 56 according to the gain characteristics, outputting the corrected control signal Sc through the D/A converter 22 to the front speaker 14, and also outputting the corrected control signal Scc through the compensation filter 66 and the D/A converter 64 to the rear speaker 15.

Figure 13:
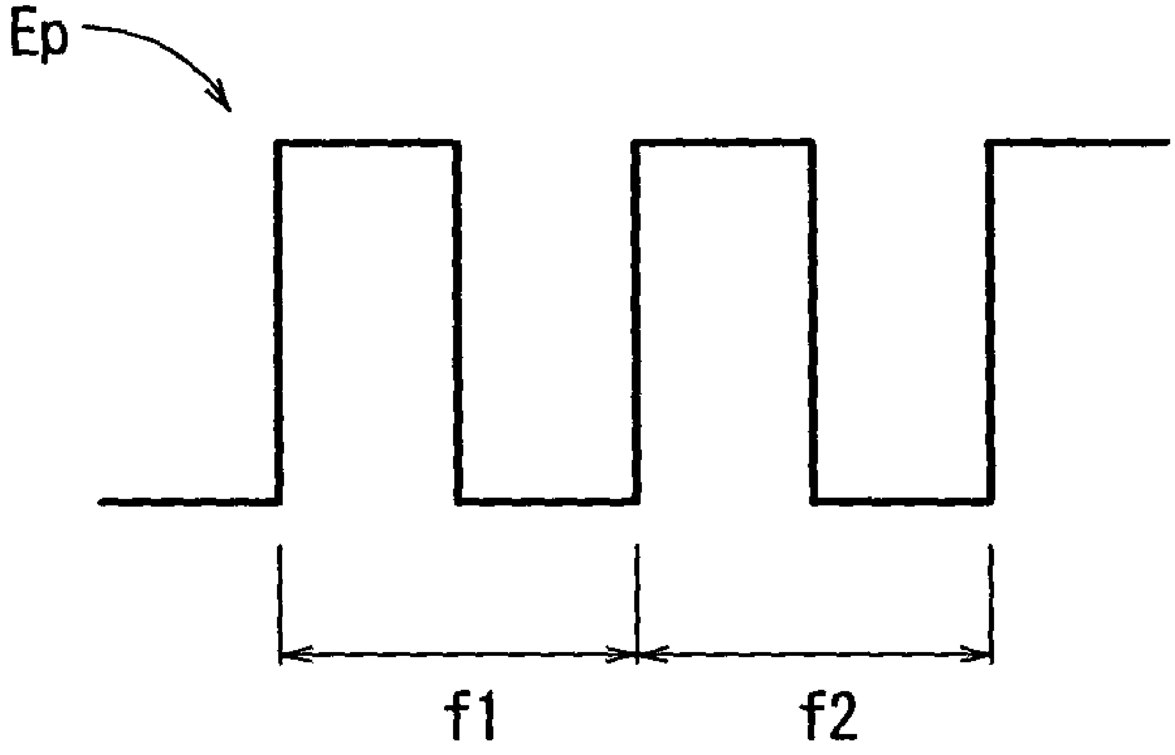
FIG. 13 is a diagram showing a waveform of engine pulses.

FIG. 13 shows the waveform of engine pulses Ep. For determining a frequency change Δaf, the frequency change detector 68 determines the difference Δf (Δf=f2−f1) between the frequencies of two successive pulses, i.e., the frequency f1 of a preceding pulse (preceding frequency) and the frequency f2 of a following pulse (present frequency), which are successively detected by the frequency detector 23, and multiplies the difference Δf by the present frequency f2 to determine a frequency change Δaf (Δaf=Δf×f2) per unit time of the engine rotation frequency fe, i.e., to determine an acceleration.

It is known in the art that the frequency change Δaf has a different value depending on which gear position the transmission of the motor vehicle is in. Specifically, the frequency change Δaf is greater when the transmission is in a lower gear position and is smaller when the transmission is in a higher gear position.

Generally, the sound level of the sound effect, which depends on the frequency change Δaf, should preferably be greater in a lower gear position than in a higher gear position. The sound level of the sound effect should preferably be lower when the motor vehicle cruises at a constant speed or is decelerated.

Figure 14:
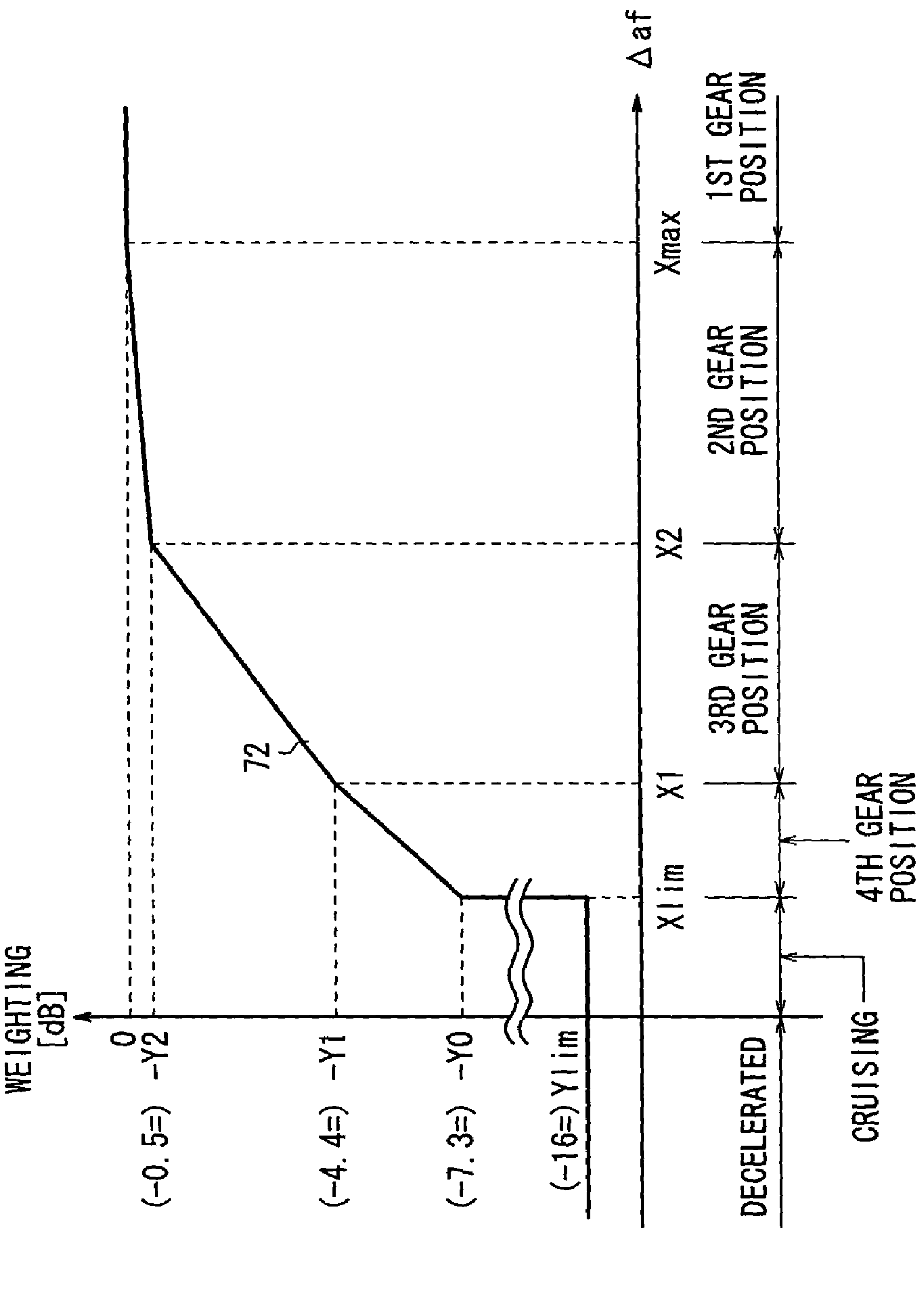
FIG. 14 is a diagram showing a weighting gain characteristic curve that is set in a sound pressure adjuster.

FIG. 14 shows a weighting gain characteristic curve 72 that is set in the sound pressure adjuster 70 in view of the above considerations. The control signal Sc from the combiner 56 is supplied to the sound pressure adjuster 70, which weights the control signal Sc into a weighted control signal Scc. If the frequency change Δaf is greater than a value Xmax which corresponds to a first gear position, i.e., a low gear position, then the weighting quantity is 0 [dB], making the control signal Sc and the weighted control signal Scc equal in value to each other.

In a second gear position, as the frequency change Δaf changes from the value Xmax to a value X2, the weighting quantity is gradually reduced from the value 0 [dB] to a value −Y2 (specifically, Y2=0.5) [dB]. In a third gear position, as the frequency change Δaf changes from the value X2 to a value X1, the weighting quantity is gradually reduced from the value −Y2 [dB] to a value −Y1 (specifically, Y1=4.4) [dB]. In a fourth gear position, as the frequency change Δaf changes from the value X1 to a value Xlim, the weighting quantity is gradually reduced from the value −Y1 [dB] to a value −Y0 (specifically, Y0=7.3) [dB]. If the frequency change Δaf is not greater than the value Xlim, it is judged that the motor vehicle is cruising or is being decelerated, and the weighting quantity is set to a constant value −Ylim (specifically, Ylim=16) [dB].

In the mobile object sound effect producing apparatus 105 according to the fifth embodiment shown in FIG. 12, the frequency change Δaf per unit time of the engine rotation frequency fe is detected, and a sound effect that is corrected by the sound pressure adjuster 70 having the gain characteristics 72 depending on the frequency change Δaf is generated. The gain characteristics 72 are set to the constant value Ylim when the frequency change Δaf is not greater than the value Xlim. Therefore, depending on the acceleration of the motor vehicle, the sound pressure level is increased to allow the passenger to feel the acceleration based on the sound effect. Inasmuch as the sound pressure level is constant when the frequency change Δaf is not greater than the value Xlim, including small accelerations and decelerations, beat sounds due to small accelerations and decelerations are prevented from occurring while the motor vehicle is cruising at a constant speed.

Figure 15:
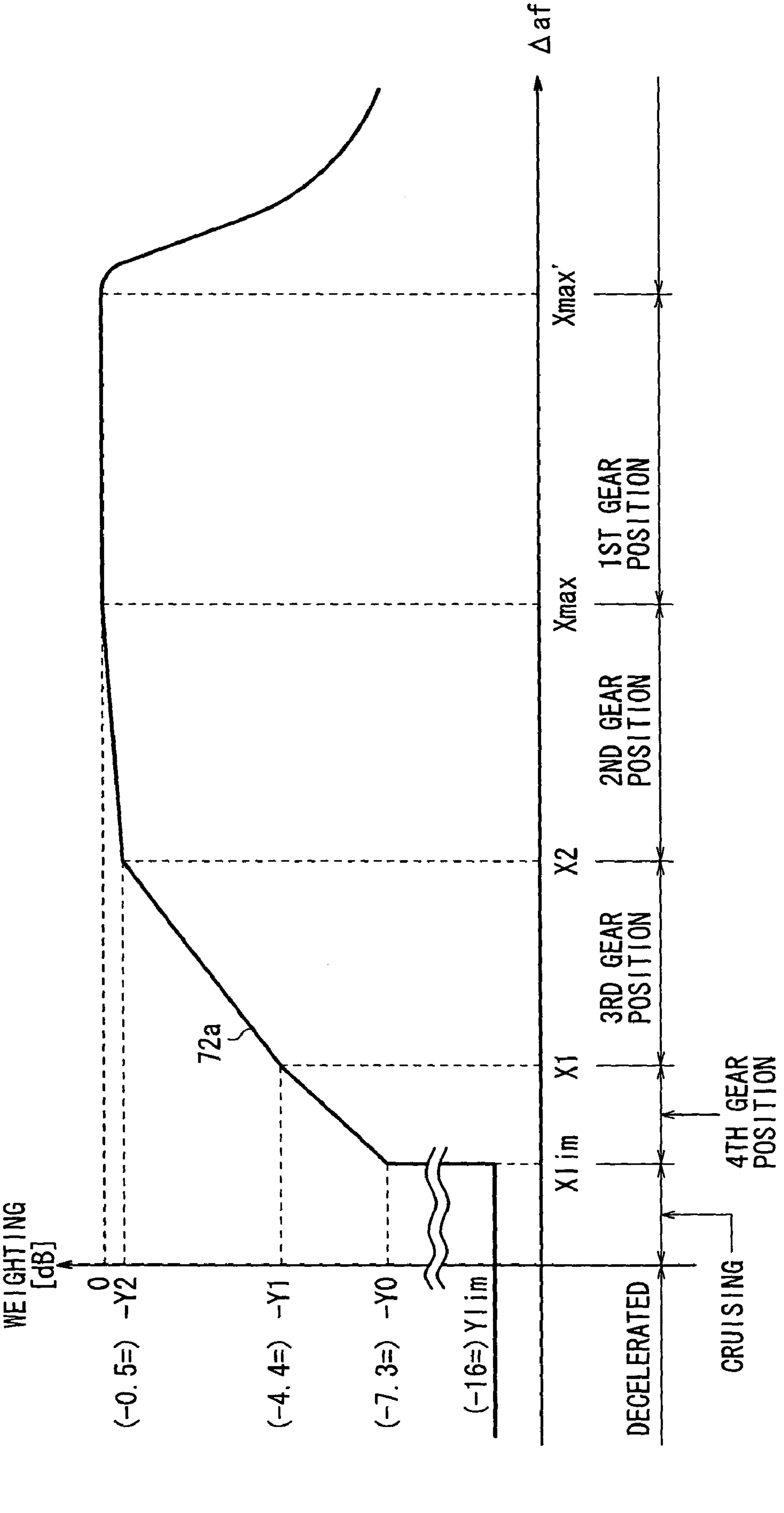
FIG. 15 is a diagram showing another weighting gain characteristic curve that is set in a sound pressure adjuster.

When the frequency change Δaf is greater than a value Xmax' which is a second predetermined value, the sound pressure adjuster 70 has a weighting gain characteristic curve 72*a* as shown in FIG. 15. According to the weighting gain characteristic curve 72*a*, the gain decreases as the frequency change Δaf increases in excess of the value Xmax'.

With the weighting gain characteristic curve 72*a*, at the time the frequency change of the engine rotation frequency increases when the engine is raced or the transmission on the mobile object has a throttle kickdown, the motor vehicle is prevented from being erroneously recognized as being fully accelerated, and a considerably large sound effect is prevented from being generated, so that the passenger in the motor vehicle will not feel strange and uncomfortable. Specifically, when the frequency change Δaf increases in excess of the value Xmax' which represents a fully open throttle position in the first gear position, the gain is reduced according to the weighting gain characteristic curve 72*a* as the frequency change Δaf increases. Accordingly, no large sound effect is produced.

In the mobile object sound effect producing apparatus 105 according to the fifth embodiment shown in FIG. 12, the sound effect generated using the frequency change detector 68 and the sound pressure adjuster 70 is radiated from the front and rear speakers 14, 15. However, the sound effect generated using the frequency change detector 68 and the sound pressure adjuster 70 may be radiated from the front speaker 14 only or the rear speaker 15 only. For example, the principles of the fifth embodiment are applicable to the mobile object sound effect producing apparatus 101 shown in FIG. 1.

Figure 16:
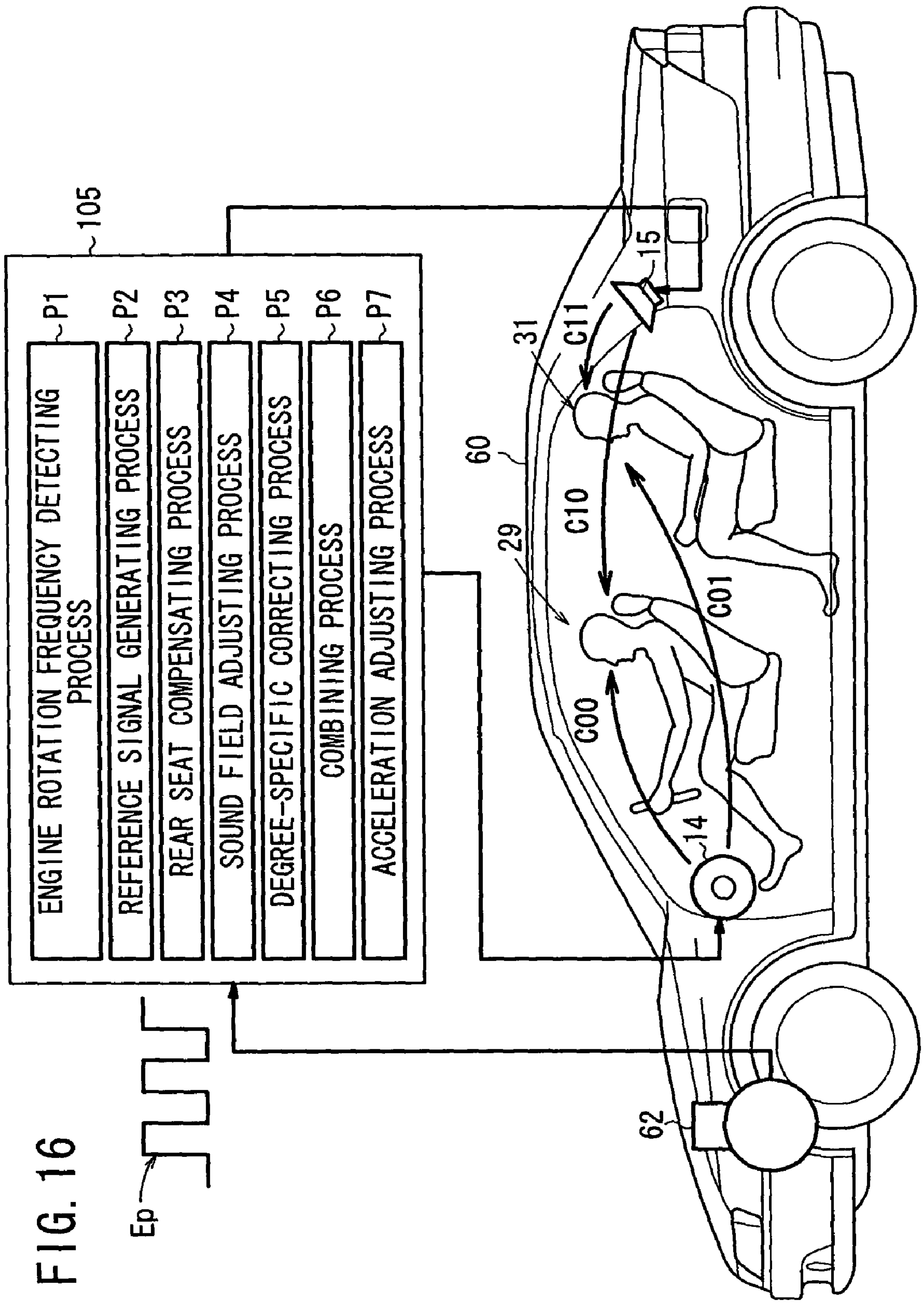
FIG. 16 is a functional block diagram of the mobile object sound effect producing apparatus according to the fifth embodiment of the present invention.

FIG. 16 shows in functional block form the mobile object sound effect producing apparatus 105 according to the fifth embodiment of the present invention. The mobile object sound effect producing apparatus 105 includes all the functions described above in the first through fourth embodiments, and will generally be described below.

When the driver in the front seat passenger position 29 depresses the accelerator pedal, the engine 62 supplies engine pulses Ep to the frequency detector 23 of the mobile object sound effect producing apparatus 105, which detects the engine rotation frequency Fe (engine rotation frequency detecting process P1).

Then, the engine rotation frequency Fe is multiplied by 4, 5, and 6 by the respective multipliers 24, 25, 26, and the multiplied frequencies are supplied to the reference signal generating means 21.

The reference signal generating means 21 refers to the waveform data table 16 and simultaneously generates sine-wave reference signals Sr1, Sr2, Sr3 of degrees 4, 5, 6 (reference signal generating process P2).

At this time, the compensation filter 66 performs a rear seat compensating process P3 such that sounds output from the speakers 14, 15 are zero at the rear seat passenger position 31.

The first acoustic correctors 51*a* operate to prevent sounds from the speakers 14, 15 from having peaks and dips due to the vehicle cabin sound field characteristics C00+F·C10 (see FIG. 11) at the front seat passenger position 29, making the sound effect at the front seat passenger position 29 linear in proportion to engine rotational speed and reducing sound effect interruptions (sound field adjusting process P4 including frequency emphasizing process). At this time, the sound pressure level within a certain frequency range may be increased or reduced by the second acoustic corrector 52.

The third acoustic correctors 53*a*, 53*b*, 53*c* adjust the gain characteristics of the respective degrees depending on the engine rotational speed f3 to control tone colors (degree-specific correcting process P5). Therefore, a sound effect of multiple degrees, depending on fuel combustion in the engine 62, can be generated.

The reference signals corrected by the acoustic control means 204 are combined into a control signal Sc by the combiner 56 (combining process P6).

The frequency change detector 68 and the sound pressure adjuster 70 detect an engine rotational speed change Δaf, and weight the control signal Sc depending on the acceleration Δaf, thereby generating a control signal Scc in which a mismatch between the accelerating action and sound quality has been removed (acceleration adjusting process P7). According to the acceleration adjusting process P7, a sound effect can be generated depending on the accelerating action of the accelerator pedal and the transmission, and generation of a sound effect can be suppressed when the motor vehicle is accelerated with the change in engine rotational speed being not greater than a certain value, when the motor vehicle cruises at a constant speed, or when the motor vehicle is decelerated.

Figure 17:
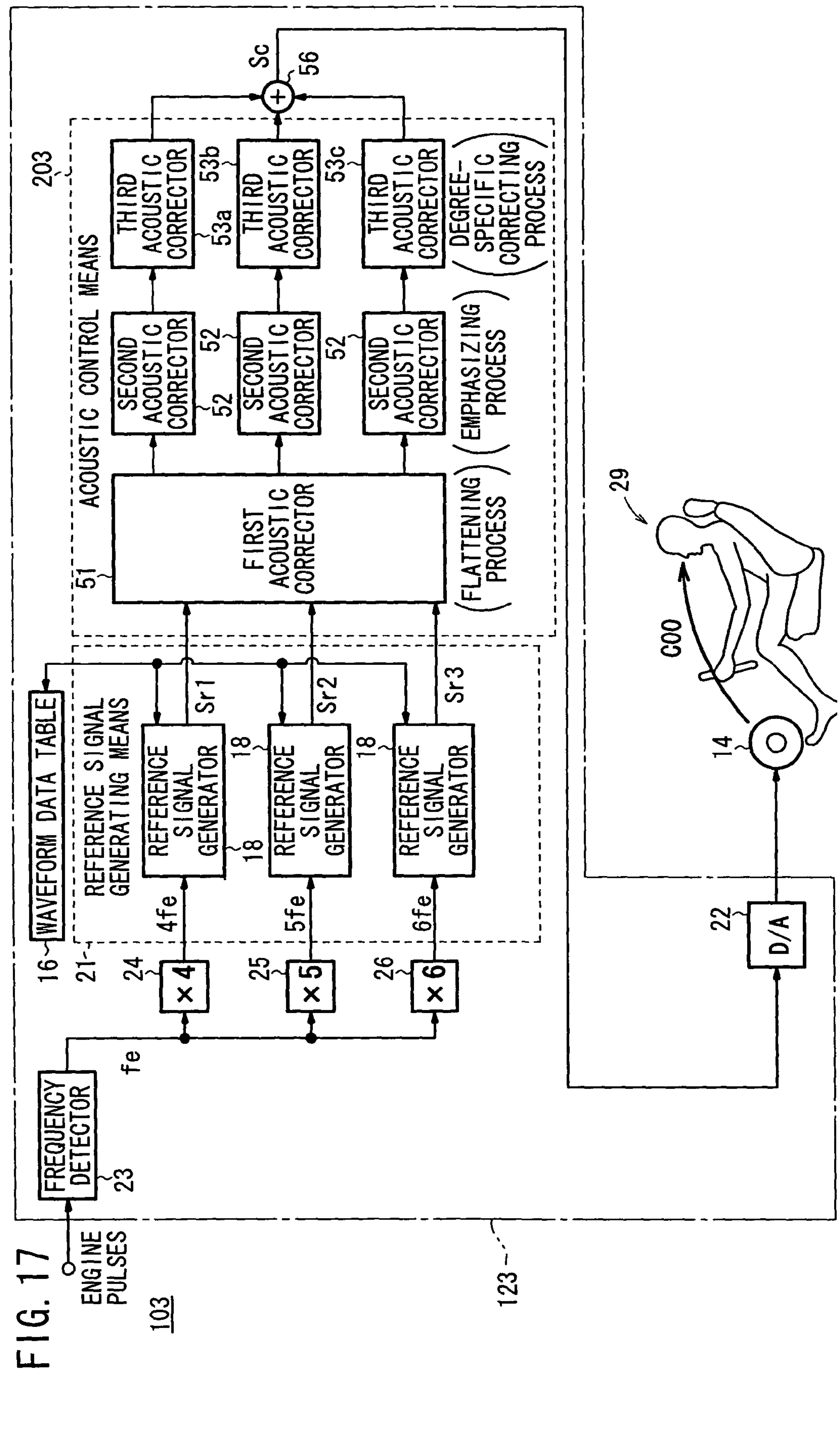
FIG. 17 is a block diagram of a modified mobile object sound effect producing apparatus.

FIG. 17 shows in block form a mobile object sound effect producing apparatus according to a modification of the mobile object sound effect producing apparatus 103 shown in FIG. 6. According to the modified mobile object sound effect producing apparatus, since the frequencies of the three reference signals Sr1, Sr2, Sr3 generated by the respective reference signal generators 18 are different from each other, the three first acoustic correctors 51 shown in FIG. 6 are replaced with a single wide-band acoustic corrector 51, which covers the frequency ranges of the three first acoustic correctors 51, for performing the flattening process.

Although certain preferred embodiments of the present invention have been shown and described in detail, it should be understood that various changes and modifications may be made therein without departing from the scope of the invention as set forth in the appended claims.

What is claimed is:

1. A mobile object sound effect producing apparatus comprising:

a waveform data table for storing waveform data in one cyclic period;

reference signal generating means for generating a reference signal, which includes a harmonic signal, based on an engine rotation frequency by successively reading the waveform data from said waveform data table;

acoustic control means for generating a control signal based on said reference signal;

output means for converting said control signal into a sound effect and outputting the sound effect;

a frequency change detector for determining a frequency change per unit time of said engine rotation frequency; and a sound pressure adjuster for correcting said control signal according to gain characteristics depending on said frequency change, and outputting the corrected control signal to said output means, wherein said gain characteristics of said sound pressure adjuster are set to a constant gain when said frequency change is not greater than a predetermined value.

2. A mobile object sound effect producing apparatus according to claim 1, wherein said acoustic control means has a first acoustic corrector for correcting, based on the engine rotation frequency, said reference signal to generate said control signal, said first acoustic corrector having gain characteristics represented by an inversion of gain characteristics which change depending on a frequency of said reference signal from said output means to a passenger position.

3. A mobile object sound effect producing apparatus according to claim 2, wherein said acoustic control means further comprises:

a second acoustic corrector for adjusting the magnitude of said reference signal within a predetermined frequency range, and said first acoustic corrector and said second acoustic corrector correct, based on the engine rotation frequency, said reference signal to generate said control signal.

4. A mobile object sound effect producing apparatus according to claim 2, wherein said reference signal generating means further comprises:

a plurality of reference signal generators for generating respective reference signals, each of which includes a harmonic signal, based on the engine rotation frequency by successively reading the waveform data from said waveform data table; and said acoustic control means further comprises:

a plurality of first acoustic correctors having respective gain characteristics represented by an inversion of gain characteristics which change depending on the frequencies of said reference signals from said output means to the passenger position;

a plurality of second acoustic correctors for adjusting the magnitudes of the reference signals of respective degrees; and a combiner for combining the reference signals which have been corrected by said first acoustic correctors and said second acoustic correctors and outputting the control signal.

5. A mobile object sound effect producing apparatus according to claim 2, wherein said output means further comprises:

a first output unit and a second output unit;

said mobile object sound effect producing apparatus further comprising:

a compensation filter for processing said control signal according to predetermined characteristics, wherein said first output unit converts said control signal into said sound effect and outputs said sound effect, and said second output unit converts said control signal which has been processed by said compensation filter into a sound effect and outputs said sound effect, and wherein said predetermined characteristics of said compensation filter comprise transfer characteristics represented by the product of −1 and the quotient produced when the transfer characteristics of an acoustic signal from said first output unit to another passenger position are divided by the transfer characteristics from said second output unit to said other passenger position.

6. A mobile object sound effect producing apparatus according to claim 2, wherein said gain characteristics of said sound pressure adjuster are set to a gain which decreases as said frequency change increases when said frequency change is greater than a second predetermined value.

7. A mobile object sound effect producing apparatus comprising:

a waveform data table for storing waveform data in one cyclic period;

reference signal generating means for generating a reference signal, which includes a harmonic signal, based on an engine rotation frequency by successively reading the waveform data from said waveform data table;

acoustic control means for generating a control signal based on said reference signal;

output means for converting said control signal into a sound effect and outputting the sound effect;

a frequency change detector for determining a frequency change per unit time of said engine rotation frequency; and a sound pressure adjuster for correcting said control signal according to gain characteristics depending on said frequency change, and outputting the corrected control signal to said output means, wherein said gain characteristics of said sound pressure adjuster are set to a gain which decreases as said frequency change increases when said frequency change is greater than a predetermined value.

8. A mobile object sound effect producing apparatus according to claim 7, wherein said acoustic control means has a first acoustic corrector for correcting, based on the engine rotation frequency, said reference signal to generate said control signal, said first acoustic corrector having gain characteristics represented by an inversion of gain characteristics which change depending on a frequency of said reference signal from said output means to a passenger position.

9. A mobile object sound effect producing apparatus according to claim 8, wherein said acoustic control means further comprises:

a second acoustic corrector for adjusting the magnitude of said reference signal within a predetermined frequency range, and said first acoustic corrector and said second acoustic corrector correct, based on the engine rotation frequency, said reference signal to generate said control signal.

10. A mobile object sound effect producing apparatus according to claim 8, wherein said reference signal generating means further comprises:

a plurality of reference signal generators for generating respective reference signals, each of which includes a harmonic signal, based on the engine rotation frequency by successively reading the waveform data from said waveform data table; and said acoustic control means further comprises:

a plurality of first acoustic correctors having respective gain characteristics represented by an inversion of gain characteristics which change depending on the frequencies of said reference signals from said output means to the passenger position;

a plurality of second acoustic correctors for adjusting the magnitudes of the reference signals of respective degrees; and a combiner for combining the reference signals which have been corrected by said first acoustic correctors and said second acoustic correctors and outputting the control signal.

11. A mobile object sound effect producing apparatus according to claim 8, wherein said output means further comprises:

a first output unit and a second output unit;

said mobile object sound effect producing apparatus further comprising:

a compensation filter for processing said control signal according to predetermined characteristics, wherein said first output unit converts said control signal into said sound effect and outputs said sound effect, and said second output unit converts said control signal which has been processed by said compensation filter into a sound effect and outputs said sound effect, and wherein said predetermined characteristics of said compensation filter comprise transfer characteristics represented by the product of −1 and the quotient produced when the transfer characteristics of an acoustic signal from said first output unit to another passenger position are divided by the transfer characteristics from said second output unit to said other passenger position.

* * * * *